(12) United States Patent
Ostertag et al.

(10) Patent No.: US 6,548,301 B2
(45) Date of Patent: Apr. 15, 2003

(54) RETROVIRAL GENE TRANSFER VECTORS

(75) Inventors: Wolfram Ostertag, Hamburg (DE); Christopher Baum, Hamburg (DE); Markus Hildinger, Hamburg (DE)

(73) Assignee: Heinrich-Pette-Institut, Hamburg (DE)

( * ) Notice: Subject to any disclaimer, the term of this patent is extended or adjusted under 35 U.S.C. 154(b) by 0 days.

(21) Appl. No.: 09/306,417

(22) Filed: May 6, 1999

(65) Prior Publication Data

US 2002/0103144 A1 Aug. 1, 2002

(30) Foreign Application Priority Data

May 8, 1998 (DE) ......................... 198 22 115

(51) Int. Cl.$^7$ .................. C12N 15/85; C12N 15/86; A61K 31/713
(52) U.S. Cl. ............. 435/455; 435/320.1; 435/235.1; 514/44
(58) Field of Search .................. 435/320.1, 235.1, 435/455; 514/44

(56) References Cited

U.S. PATENT DOCUMENTS 5,858,744 A * 1/1999 Baum et al. ............. 435/172.3

FOREIGN PATENT DOCUMENTS

WO   WO 92/07943   *  5/1992   ........... C12N/15/63

OTHER PUBLICATIONS

Orkin, et al. :Report and Recommendations of the Panel to Assess the NIH Investment in Research on Gene Therapy, www.nih.gov Dec. 1995.*

Verma et al. :Gene Therapy—promises, problems and prospects, Nature vol 389, Sep. 1997, p. 239–242.*

Nevin, et al. Supervision and Obstacles to Gene Therapy: International Journal of Pharmaceutical Medicine, 12: (1998)p. 19–22.*

* cited by examiner

Primary Examiner—James Ketter
Assistant Examiner—Daniel M Sullivan
(74) Attorney, Agent, or Firm—Nixon & Vanderhye PC

(57) ABSTRACT

The invention relates to novel retroviral gene transfer vectors, preferably expression vectors, which, because of a reduced content of viral genes, are distinguished by a higher safety standard and an expression of non-viral nucleotide sequences in higher amounts.

33 Claims, 8 Drawing Sheets

SEQUENCE LISTING

```
<160> NUMBER OF SEQ ID NOS: 17

<210> SEQ ID NO 1
<211> LENGTH: 8630
<212> TYPE: DNA
<213> ORGANISM: Artificial Sequence
<220> FEATURE:
<223> OTHER INFORMATION: Description of Artificial Sequence: proviral
      plasmid DNA
<220> FEATURE:
<221> NAME/KEY: misc_feature
<222> LOCATION: (1)..(160)
<223> OTHER INFORMATION: plasmid backbone (pUC)
<220> FEATURE:
<221> NAME/KEY: misc_feature
<222> LOCATION: (161)..(677)
<223> OTHER INFORMATION: 5'-LTR
<220> FEATURE:
<221> NAME/KEY: 5'UTR
<222> LOCATION: (532)..(1219)
<220> FEATURE:
<221> NAME/KEY: mat_peptide
<222> LOCATION: (1220)..(5062)
<223> OTHER INFORMATION: m4 mdr-1 cDNA
<220> FEATURE:
<221> NAME/KEY: misc_feature
<222> LOCATION: (5215)..(5774)
<223> OTHER INFORMATION: 3'-LTR
<220> FEATURE:
<221> NAME/KEY: misc_feature
<222> LOCATION: (5775)..(8630)
<223> OTHER INFORMATION: plasmid backbone (pUC)
<220> FEATURE:
<221> NAME/KEY: misc_feature
<222> LOCATION: (1)..(8630)
<223> OTHER INFORMATION: retroviral expression vector SFbeta71m4

<400> SEQUENCE: 1 tcgaggggggg gcccggtcac gattagtcca atttgttaaa gacaggatat cagtggtcca       60
ggctctagtt ttgactcaac aatatcacca gctgaagcct atagagtacg agccatagat      120
agaataaaag attttattta gtctccagaa aaggggggga atgaaagacc ccacctgtag      180
gtttggcaag ctagcttaag taacgccatt ttgcaaggca tggaaaatac ataactgaga      240
atagagaagt tcagatcaag gttaggaaca gagagacagc agaatatggg ccaaacagga      300
```

-continued

| | | | | |
|---|---|---|---|---|
| tatctgtggt | aagcagttcc | tgccccgctc | agggccaaga | acagatggtc | cccagatgcg | 360 |
| gtcccgccct | cagcagtttc | tagagaacca | tcagatgttt | ccagggtgcc | ccaaggacct | 420 |
| gaaaatgacc | ctgtgcctta | tttgaactaa | ccaatcagtt | cgcttctcgc | ttctgttcgc | 480 |
| gcgcttctgc | tccccgagct | caataaaaga | gcccacaacc | cctcactcgg | cgcgccagtc | 540 |
| ctccgattga | ctgagtcgcc | cggg taccccg | tattcccaat | aaagcctctt | gctgtttgca | 600 |
| tccgaatcgt | ggactcgctg | atccttggga | gggtctcctc | agattgattg | actgcccacc | 660 |
| tcggggtct | ttcatttgga | ggttccaccg | agatttggag | acccctgccc | agggaccacc | 720 |
| gaccccccg | ccgggaggta | agctggccag | cggtcgtttc | gtgtctgtct | ctgtctttgt | 780 |
| gcgtgtttgt | gccggcatct | aatgtttgcg | cctgcgtctg | tactagttgg | ctaactagat | 840 |
| ctgtatctgg | cggtcccgcg | gaagaactga | cgagttcgta | ttcccggccg | cagcccctgg | 900 |
| gagacgtccc | agcggcctcg | ggggcccgtt | ttgtggccca | ttctgtatca | gttaacctac | 960 |
| ccgagtcgga | ctttttggag | ctccgccact | gtccgagggg | tacgtggctt | tgttgggga | 1020 |
| cgagagacag | agacacttcc | cgcccccgtc | tgaattttttg | ctttcggttt | tacgccgaaa | 1080 |
| ccgcgccgcg | cgtcttgtct | gctgcagcat | cgttctgtgt | tgtctctgtc | tgactgtgtt | 1140 |
| tctgtatttg | tctgaaaatt | agctcgacaa | agttaactaa | tagtccctct | ctccaagctc | 1200 |
| acttacaggc | gcggccgcca | tggatcttga | aggggaccgc | aatggaggag | caagaagaa | 1260 |
| gaacttttt | aaactgaaca | ataaaagtga | aaagataag | aaggaaaaga | aaccaactgt | 1320 |
| cagtgtattt | tcaatgtttc | gctattcaaa | ttggcttgac | aagttgtata | tggtggtggg | 1380 |
| aactttggct | gccatcatcc | atggggctgg | acttcctctc | atgatgctgg | tgtttggaga | 1440 |
| aatgacagat | atcttttgcaa | atgcaggaaa | tttagaagat | ctgatgtcaa | acatcactaa | 1500 |
| tagaagtgat | atcaatgata | cagggttctt | catgaatctg | gaggaagaca | tgaccagata | 1560 |
| tgcctattat | tacagtggaa | ttggtgctgg | ggtgctggtt | gctgcttaca | ttcaggtttc | 1620 |
| attttggtgc | ctggcagctg | gaagacaaat | acacaaaatt | agaaaacagt | ttttcatgc | 1680 |
| tataatgcga | caggagatag | gctggtttga | tgtgcacgat | gttggggagc | ttaacacccg | 1740 |
| acttacagat | gatgtctcta | agattaatga | agttattggt | gacaaaattg | gaatgttctt | 1800 |
| tcagtcaatg | gcaacatttt | tcactgggtt | tatagtagga | tttacacgtg | gttgggaagct | 1860 |
| aacccttgtg | atttttggcca | tcagtcctgt | tcttggactg | tcagctgctg | tctgggcaaa | 1920 |
| gatactatct | tcatttactg | ataaagaact | cttagcgtat | gcaaaagctg | gagcagtagc | 1980 |
| tgaagaggtc | ttggcagcaa | ttagaactgt | gattgcattt | ggaggacaaa | agaaagaact | 2040 |
| tgaaggtac | aacaaaaatt | tagaagaagc | taaaagaatt | gggataaaga | aagctattac | 2100 |
| agccaatatt | tctataggtg | ctgctttcct | gctgatctat | gcatcttatg | ctctggcctt | 2160 |
| ctggtatggg | accaccttgg | tcctctcagg | ggaatattct | attggacaag | tactcactgt | 2220 |
| attcttttct | gtattaattg | gggcttttag | tgttggacag | gcatctccaa | gcattgaagc | 2280 |
| atttgcaaat | gcaagaggag | cagcttatga | aatcttcaag | ataattgata | taagccaag | 2340 |
| tattgacagc | tattcgaaga | gtgggcacaa | accagataat | attaagggaa | atttggaatt | 2400 |
| cagaaatgtt | cacttcagtt | acccatctcg | aaaagaagtt | aagatcttga | agggcctgaa | 2460 |
| cctgaaggtg | cagagtgggc | agacggtggc | cctggttgga | aacagtggct | gtgggaagag | 2520 |
| cacaacagtc | cagctgatgc | agaggctcta | tgaccccaca | gaggggatgg | tcagtgttga | 2580 |
| tggacaggat | attaggacca | taaatgtaag | gtttctacgg | gaaatcattg | gtgtggtgag | 2640 |
| tcaggaacct | gtattgtttg | ccaccacgat | agctgaaaac | attcgctatg | gccgtgaaaa | 2700 |

-continued

```
tgtcaccatg gatgagattg agaaagctgt caaggaagcc aatgcctatg actttatcat   2760
gaaactgcct cataaatttg acaccctggt tggagagaga ggggcccagt tgagtggtgg   2820
gcagaagcag aggatcgcca ttgcacgtgc cctggttcgc aaccccaaga tcctcctgct   2880
ggatgaggcc acgtcagcct tggacacaga aagcgaagca gtggttcagg tggctctgga   2940
taaggccaga aaggtcggac caccattgtg atagctcatc gtttgtctac agttcgtaa    3000 tgctgacgtc atcgctggtt tcgatgatgg agtcattgtg gagaaaggaa atcatgatga   3060
actcatgaaa gagaaaggca tttacttcaa acttgtcaca atgcagacag caggaaatga   3120
agttgaatta gaaatgcagc tgatgaatcc aaaagtgaaa attgatgcct tggaaatgtc   3180
ttcaaatgat tcaagatcca gtctaataag aaaaagatca actcgtagga gtgtccgtgg   3240
atcacaagcc caagacagaa agcttagtac caagagggct ctggatgaaa gtatacctcc   3300
agtttccttt tggaggatta tgaagctaaa tttaactgaa tggccttatt tgttgttgg    3360 tgtattttgt gccattataa atggaggcct gcaaccagca tttgcaataa tattttcaaa   3420
gattataggg gttttacaa gaattgatga tcctgaaaca aaacgacaga atagtaactt    3480
gttttcacta ttgtttctag cccttggaat tatttctttt attacatttt ccttcaagg    3540 tttcacattt ggcaaagctg gagagatcct caccaagcgg ctccgataca tggttttccg   3600
atccatgctc agacaggatg tgagttggtt tgatgaccct aaaaacacca ctggagcatt   3660
gactaccagg ctcgccaatg atgctgctca agttaaaggg gctataggtt ccaggcttgc   3720
tgtaattacc cagaatatag caaatcttgg gacaggaata attatatcct tcatctatgg   3780
ttggcaacta acactgttac tcttagcaat tgtacccatc attgcaatag caggagttgt   3840
tgaaatgaaa atgttgtctg acaagcact gaaagataag aaagaactag aaggtgctgg    3900
gaagatcgct actgaagcaa tagaaaaactt ccgaaccgtt gtttctttga ctcaggagca   3960
gaagtttgaa catatgtatg ctcagagttt gcaggtacca tacagaaact ctttgaggaa   4020
agcacacatc tttggaatta catttttcctt cacccaggca atgatgtatt tttcctatgc   4080
tggatgtttc cggtttggag cctacttggt ggcacataaa ctcatgagct ttgaggatgt   4140
tctgttagta ttttcagctg ttgtctttgg tgccatggcc gtggggcaag tcagttcatt   4200
tgctcctgac tatgccaaag ccaaaatatc agcagcccac atcatcatga tcattgaaaa   4260
aacccctttg attgacagct acagcacgga aggcctaatg ccgaacacat tggaaggaaa   4320
tgtcacattt ggtgaagttg tattcaacta tcccacccga ccggacatcc cagtgcttca   4380
gggactgagc ctgaggtga agagggcca gacgctggct ctggtgggca gcagtggctg    4440
tgggaagagc acagtggtcc agctcctgga gcggttctac gaccccttgg cagggaaagt   4500
gctgcttgat ggcaaagaaa ttaagcgact gaatgttcag tggctccgag cacacctggg   4560
catcgtgtcc caggagccca tcctgtttga ctgcagcatt gctgagaaca ttgcctatgg   4620
agacaacagc cgggtggtgt cacaggaaga gatcgtgagg gcagcaaagg aggccaacat   4680
acatgccttc atcgagtcac tgcctaataa atatagcact aaagtaggag acaaaggaac   4740
tcagctctct ggtggccaga acaacgcat tgccatagct cgtgcccttg ttagacagcc    4800
tcatattttg cttttggatg aagccacgtc agctctggat acagaaagtg aaaaggttgt   4860
ccaagaagcc ctggacaaag ccagagaagg ccgcacctgc attgtgattg ctcaccgcct   4920
gtccaccatc cagaatgcag acttaatagt ggtgttcag aatggcagag tcaaggagca    4980
tggcacgcat cagcagctgc tggcacagaa aggcatctat ttttcaatgg tcagtgtcca   5040
```

```
ggctggaaca aagcgccagt gaactctgac tgtatgagat gttaaatact ttttaatggg   5100
gatccaagct tatcgatagg cctaggccta tcgataggcc taggcctatc gataggccta   5160
acacgagcca tagatagaat aaaagatttt atttagtctc cagaaaaagg ggggaatgaa   5220
agaccccacc tgtaggtttg gcaagctagc tgcagtaacg ccattttgca aggcatggaa   5280
aaataccaaa ccaagaatag agaagttcag atcaagggcg ggtacatgaa aatagctaac   5340
gttgggccaa acaggatatc tgcggtgagc agtttcggcc ccggcccggg gccaagaaca   5400
gatggtcacc gcagtttcgg ccccggcccg aggccaagaa cagatggtcc ccagatatgg   5460
cccaaccctc agcagtttct taagacccat cagatgtttc caggctcccc caaggacctg   5520
aaatgaccct gcgccttatt tgaattaacc aatcagcctg cttctcgctt ctgttcgcgc   5580
gcttctgctt cccgagctct ataaaagagc tcacaacccc tcactcggcg cgccagtcct   5640
ccgattgact gagtcgcccg ggtacccgta ttcccaataa agcctcttgc tgtttgcatc   5700
cgaatcgtgg actcgctgat ccttgggagg gtctcctcag attgattgac tgcccacctc   5760
ggggtctttc agtaggatc tcgaccgatg cccttgagag ccttcaaccc agtcagctcc   5820
ttccggtggg cgcggggcat gactatcgtc gccgcactta tgactgtctt ctttatcatg   5880
caactcgtag gacaggtgcc ggcagcgctc tgggtcattt tcggcgagga ccgctttcgc   5940
tggagcgcga cgatgatcgg cctgtcgctt gcggtattcg gaatcttgca cgccctcgct   6000
caagccttcg tcactggtcc cgccaccaaa cgtttcggcg agaagcaggc cattatcgcc   6060
ggcatggcgg ccgacgcgct gggctacgtc ttgctggcgt tcgcgacgcg aggctggatg   6120
gccttcccca ttatgattct tctcgcttcc ggcggcatcg gatgcccgc gttgcaggcc   6180
atgctgtcca ggcaggtaga tgacgaccat cagggacagc ttcaaggatc gctcgcggct   6240
cttaccagcc taacttcgat cattggaccg ctgatcgtca cggcgattta tgccgcctcg   6300
gcgagcacat ggaacgggtt ggcatggatt gtaggcgcct gatgcggtat tttctcctta   6360
cgcatctgtg cggtatttca caccgcatat ggtgcactct cagtacaatc tgctctgatg   6420
ccgcatagtt aagccagccc cgacacccgc caacacccgc tgacgcgccc tgacgggctt   6480
gtctgctccc ggcatccgct tacagacaag ctgtgaccgt ctccgggagc tgcatgtgtc   6540
agaggttttc accgtcatca ccgaaacgcg cgagacgaaa gggcctcgtg atacgcctat   6600
ttttataggt taatgtcatg ataataatgg tttcttagac gtcaggtggc acttttcggg   6660
gaaatgtgcg cggaacccct atttgtttat ttttctaaat acattcaaat atgtatccgc   6720
tcatgagaca ataaccctga taaatgcttc aataatattg aaaaaggaag agtatgagta   6780
ttcaacattt ccgtgtcgcc cttattccct ttttgcggc attttgcctt cctgtttttg   6840
ctcacccaga aacgctggtg aaagtaaaag atgctgaaga tcagttgggt gcacgagtgg   6900
gttacatcga actggatctc aacagcggta agatccttga gttttcgc cccgaagaac   6960
gttttccaat gatgagcact tttaaagttc tgctatgtgg cgcggtatta tcccgtattg   7020
acgccgggca agagcaactc ggtcgccgca tacactattc tcagaatgac ttggttgagt   7080
actcaccagt cacagaaaag catcttacgg atggcatgac agtaagagaa ttatgcagtg   7140
ctgccataac catgagtgat aacactgcgg ccaacttact tctgacaacg atcggaggac   7200
cgaaggagct aaccgctttt ttgcacaaca tgggggatca tgtaactcgc cttgatcgtt   7260
gggaaccgga gctgaatgaa gccataccaa acgacgagcg tgacaccacg atgcctgtag   7320
caatggcaac aacgttgcgc aaactattaa ctggcgaact acttactcta gcttcccggc   7380
aacaattaat agactggatg gaggcggata aagttgcagg accacttctg cgctcggccc   7440
```

-continued

```
ttccggctgg ctggtttatt gctgataaat ctggagccgg tgagcgtggg tctcgcggta    7500
tcattgcagc actggggcca gatggtaagc cctcccgtat cgtagttatc tacacgacgg    7560
ggagtcaggc aactatggat gaacgaaata gacagatcgc tgagataggt gcctcactga    7620
ttaagcattg gtaactgtca gaccaagttt actcatatat actttagatt gatttaaaac    7680 ttcatttta atttaaaagg atctaggtga agatccttt tgataatctc atgaccaaaa    7740
tcccttaacg tgagttttcg ttccactgag cgtcagaccc cgtagaaaag atcaaaggat    7800
cttcttgaga tcctttttt ctgcgcgtaa tctgctgctt gcaaacaaaa aaaccaccgc    7860
taccagcggt ggtttgtttg ccggatcaag agctaccaac tcttttccg aaggtaactg    7920 gcttcagcag agcgcagata ccaaatactg tccttctagt gtagccgtag ttaggccacc    7980
acttcaagaa ctctgtagca ccgcctacat acctcgctct gctaatcctg ttaccagtgg    8040
ctgctgccag tggcgataag tcgtgtctta ccgggttgga ctcaagacga tagttaccgg    8100
ataaggcgca gcggtcgggc tgaacggggg gttcgtgcac acagcccagc ttggagcgaa    8160
cgacctacac cgaactgaga tacctacagc gtgagcattg agaaagcgcc acgcttcccg    8220
aagggagaaa ggcggacagg tatccggtaa gcggcagggt cggaacagga gagcgcacga    8280
gggagcttcc agggggaaac gcctggtatc tttatagtcc tgtcgggttt cgccacctct    8340
gacttgagcg tcgatttttg tgatgctcgt caggggggcg gagcctatgg aaaaacgcca    8400
gcaacgcggc cttttacgg ttcctggcct tttgctggcc ttttgctcac atgttctttc    8460
ctgcgttatc ccctgattct gtggataacc gtattaccgc ctttgagtga gctgataccg    8520
ctcgccgcag ccgaacgacc gagcgcagcg agtcagtgag cgaggaagcg gaagagcgcc    8580
caatacgcaa accgcctctc cccgcgcgtt ggccgattca ttaatgcagg               8630
```

<210> SEQ ID NO 2
<211> LENGTH: 8630
<212> TYPE: DNA
<213> ORGANISM: Artificial Sequence
<220> FEATURE:
<223> OTHER INFORMATION: Description of Artificial Sequence: proviral
      plasmid DNA
<220> FEATURE:
<221> NAME/KEY: misc_feature
<222> LOCATION: (1)..(8630)
<223> OTHER INFORMATION: retroviral expression vector SFbeta91mSA1
<220> FEATURE:
<221> NAME/KEY: misc_feature
<222> LOCATION: (1)..(160)
<223> OTHER INFORMATION: plasmid backbone (pUC)
<220> FEATURE:
<221> NAME/KEY: misc_feature
<222> LOCATION: (161)..(677)
<223> OTHER INFORMATION: 5'-LTR
<220> FEATURE:
<221> NAME/KEY: 5'UTR
<222> LOCATION: (532)..(1219)
<220> FEATURE:
<221> NAME/KEY: mat_peptide
<222> LOCATION: (1220)..(5062)
<223> OTHER INFORMATION: mSA1 mdr1 cDNA
<220> FEATURE:
<221> NAME/KEY: misc_feature
<222> LOCATION: (5215)..(5774)
<223> OTHER INFORMATION: 3'-LTR
<220> FEATURE:
<221> NAME/KEY: misc_feature
<222> LOCATION: (5775)..(8630)
<223> OTHER INFORMATION: plasmid backbone (pUC)

<400> SEQUENCE: 2

-continued

| | |
|---|---|
| tcgaggggggg gcccggtcac gattagtcca atttgttaaa gacaggatat cagtggtcca | 60 |
| ggctctagtt ttgactcaac aatatcacca gctgaagcct atagagtacg agccatagat | 120 |
| agaataaaag attttattta gtctccagaa aaggggggga atgaaagacc ccacctgtag | 180 |
| gtttggcaag ctagcttaag taacgccatt ttgcaaggca tggaaaatac ataactgaga | 240 |
| atagagaagt tcagatcaag gttaggaaca gagagacagc agaatatggg ccaaacagga | 300 |
| tatctgtggt aagcagttcc tgccccgctc agggccaaga acagatggtc cccagatgcg | 360 |
| gtcccgccct cagcagtttc tagagaacca tcagatgttt ccagggtgcc caaggacct | 420 |
| gaaaatgacc ctgtgcctta tttgaactaa ccaatcagtt cgcttctcgc ttctgttcgc | 480 |
| gcgcttctgc tccccgagct caataaaaga gcccacaacc cctcactcgg cgcgccagtc | 540 |
| ctccgattga ctgagtcgcc cgggtacccg tattcccaat aaagcctctt gctgtttgca | 600 |
| tccgaatcgt ggactcgctg atccttggga ggtctcctc agattgattg actgcccacc | 660 |
| tcggggtct ttcatttgga ggttccaccg agatttggag acccctgccc agggaccacc | 720 |
| gacccccccg ccgggaggta agctggccag cggtcgtttc gtgtctgtct ctgtctttgt | 780 |
| gcgtgtttgt gccggcatct agtgtttgcg cctgcgtctg tactagttgg ctaactagat | 840 |
| ctgtatctgg cggtcccgcg gaagaactga cgagttcgta ttcccggccg cagcccctgg | 900 |
| gagacgtccc agcggcctcg ggggcccgtt ttgtggccca ttctgtatca gttaacctac | 960 |
| ccgagtcgga cttttggag ctccgccact gtccgagggg tacgtggctt tgttggggga | 1020 |
| cgagagacag agacacttcc cgcccccgtc tgaattttttg ctttcggttt tacgccgaaa | 1080 |
| ccgcgccgcg cgtcttgtct gctgcagcat cgttctgtgt tgtctctgtc tgactgtgtt | 1140 |
| tctgtatttg tctgaaaatt agctcgacaa agttaactaa tagtccctct ctccaagctc | 1200 |
| acttacaggc gcggccgcca tggatcttga aggggaccgc aatggaggag caaagaagaa | 1260 |
| gaactttttt aaactgaaca ataaaagtga aaagataag aaggaaaaga accaactgt | 1320 |
| cagtgtattt tcaatgtttc gctattcaaa ttggcttgac aagttgtata tggtggtggg | 1380 |
| aactttggct gccatcatcc atggggctgg acttcctctc atgatgctgg tgtttggaga | 1440 |
| aatgacagat atctttgcaa atgcaggaaa tttagaagat ctgatgtcaa acatcactaa | 1500 |
| tagaagtgat atcaatgata cagggttctt catgaatctg gaggaagaca tgaccaggta | 1560 |
| tgcctattat tacagtggaa ttggtgctgg ggtgctggtt gctgcttaca ttcaggtttc | 1620 |
| attttggtgc ctggcagctg gaagacaaat acacaaaatt agaaaacagt ttttttcatgc | 1680 |
| tataatgcga caggagatag gctggtttga tgtgcacgat gttggggagc ttaacacccg | 1740 |
| acttacagat gatgtctcta agattaatga agttattggt gacaaaattg gaatgttctt | 1800 |
| tcagtcaatg gcaacatttt tcactggggtt tatagtagga tttacacgtg gttggaagct | 1860 |
| aacccttgtg attttggcca tcagtcctgt tcttggactg tcagctgctg tctgggcaaa | 1920 |
| gatactatct tcatttactg ataaagaact cttagcgtat gcaaaagctg gagcagtagc | 1980 |
| tgaagaggtc ttggcagcaa ttagaactgt gattgcattt ggaggacaaa agaaagaact | 2040 |
| tgaaaggtac aacaaaaatt tagaagaagc taaaagaatt gggataaaga agctattac | 2100 |
| agccaatatt tctataggtg ctgctttcct gctgatctat gcatcttatg ctctggcctt | 2160 |
| ctggtatggg accaccttgg tcctctcagg ggaatattct attggacaag tactcactgt | 2220 |
| attcttttct gtattaattg gggcttttag tgttggacag gcatctccaa gcattgaagc | 2280 |
| atttgcaaat gcaagaggag cagcttatga aatcttcaag ataattgata taagccaag | 2340 |
| tattgacagc tattcgaaga gtgggcacaa accagataat attaagggaa atttggaatt | 2400 |

-continued

```
cagaaatgtt cacttcagtt acccatctcg aaaagaagtt aagatcttga agggcctgaa    2460
cctgaaggtg cagagtgggc agacggtggc cctggttgga aacagtggct gtgggaagag    2520
cacaacagtc cagctgatgc agaggctcta tgacccccaca gaggggatgg tcagtgttga    2580
tggacaggat attaggacca taaatgtaag gtttctacgg gaaatcattg gtgtggtgag    2640
tcaggaacct gtattgtttg ccaccacgat agctgaaaac attcgctatg gccgtgaaaa    2700
tgtcaccatg gatgagattg agaaagctgt caaggaagcc aatgcctatg actttatcat    2760
gaaactgcct cataaatttg acaccctggt tggagagaga ggggcccagt tgagtggtgg    2820
gcagaagcag aggatcgcca ttgcacgtgc cctggttcgc aaccccaaga tcctcctgct    2880
ggatgaggcc acgtcagcct ggacacagaa agcgaagca gtggttcagg tggctctgga     2940
taaggccaga aaggtcgga ccaccattgt gatagctcat cgtttgtcta cagttcgtaa     3000
tgctgacgtc atcgctggtt tcgatgatgg agtcattgtg gagaaaggaa atcatgatga    3060
actcatgaaa gagaaaggca tttacttcaa acttgtcaca atgcagacag caggaaatga    3120
agttgaatta gaaaatgcag ctgatgaatc caaagtgaa attgatgcct tggaaatgtc     3180
ttcaaatgat tcaagatcca gtctaataag aaaaagatca actcgtagga gtgtccgtgg    3240
atcacaagcc caagacagaa gcttagtac caaagaggct ctggatgaaa gtatacctcc     3300
agtttccttt tggaggatta tgaagctaaa tttaactgaa tggccttatt tgttgttgg     3360 tgtattttgt gccattataa atggaggcct gcaaccagca tttgcaataa tattttcaaa    3420
gattataggg gtttttacaa gaattgatga tcctgaaaca aaacgacaga atagtaactt    3480
gttttcacta ttgtttctag cccttggaat tatttctttt attacatttt tccttcaagg    3540
tttcacattt ggcaaagctg gagagatcct caccaagcgg ctccgataca tggttttccg    3600
atccatgctc agacaggatg tgagttggtt tgatgaccct aaaaacacca ctggagcatt    3660
gactaccagg ctcgccaatg atgctgctca gttaaaggg gctataggtt ccaggcttgc     3720
tgtaattacc cagaatatag caaatcttgg gacaggaata attatatcct tcatctatgg    3780
ttggcaacta acactgttac tcttagcaat tgtacccatc attgcaatag caggagttgt    3840
tgaaatgaaa atgttgtctg gacaagcact gaaagataag aaagaactag aaggtgctgg    3900
gaagatcgct actgaagcaa tagaaaactt ccgaaccgtt gtttctttga ctcaggagca    3960
gaagtttgaa catatgtatg ctcagagttt gcaggtacca tacagaaact ctttgaggaa    4020
agcacacatc tttggaatta cattttcctt cacccaggca atgatgtatt tttcctatgc    4080
tggatgtttc cggttggag cctacttggt ggcacataaa ctcatgagct ttgaggatgt     4140
tctgttagta ttttcagctg ttgtctttgg tgccatggcc gtggggcaag tcagttcatt    4200
tgctcctgac tatgccaaag ccaaaatatc agcagcccac atcatcatga tcattgaaaa    4260 aaccccttg attgacagct acagcacgga aggcctaatg ccgaacacat ggaaggaaa     4320 tgtcacattt ggtgaagttg tattcaacta tcccacccga ccggacatcc cagtgcttca    4380
gggactgagc ctgaggtga agaagggcca gacgctggct ctggtgggca gcagtggctg     4440
tgggaagagc acagtggtcc agctcctgga gcggttctac gaccccttgg cagggaaagt    4500
gctgcttgat ggcaaagaaa taagcgact gaatgttcag tggctccgag cacacctggg    4560
catcgtgtcc caggagccca tcctgtttga ctgcagcatt gctgagaaca ttgcctatgg    4620
agacaacagc cgggtggtgt cacaggaaga gatcgtgagg gcagcaaagg aggccaacat    4680
acatgccttc atcgagtcac tgcctaataa atatagcact aaagtaggag acaaaggaac    4740
```

```
tcagctctct ggtggccaga acaacgcat tgccatagct cgtgcccttg ttagacagcc    4800
tcatatttg cttttggatg aagccacgtc agctctggat acagaaagtg aaaaggttgt    4860
ccaagaagcc ctggacaaag ccagagaagg ccgcacctgc attgtgattg ctcaccgcct    4920
gtccaccatc cagaatgcag acttaatagt ggtgtttcag aatggcagag tcaaggagca    4980
tggcacgcat cagcagctgc tggcacagaa aggcatctat ttttcaatgg tcagtgtcca    5040
ggctggaaca aagcgccagt gaactctgac tgtatgagat gttaaatact ttttaatggg    5100
gatccaagct tatcgatagg cctaggccta tcgataggcc taggcctatc gataggccta    5160
acacgagcca tagatagaat aaaagatttt atttagtctc cagaaaaagg ggggaatgaa    5220
agacccacc tgtaggtttg gcaagctagc tgcagtaacg ccattttgca aggcatggaa    5280
aaataccaaa ccaagaatag agaagttcag atcaagggcg ggtacatgaa aatagctaac    5340
gttgggccaa acaggatatc tgcggtgagc agtttcggcc ccggcccggg ccaagaaca    5400
gatggtcacc gcagtttcgg ccccggcccg aggccaagaa cagatggtcc ccagatatgg    5460
cccaaccctc agcagtttct taagacccat cagatgtttc caggctcccc caaggacctg    5520
aaatgaccct gcgccttatt tgaattaacc aatcagcctg cttctcgctt ctgttcgcgc    5580
gcttctgctt cccgagctct ataaagagc tcacaacccc tcactcggcg cgccagtcct    5640
ccgattgact gagtcgcccg ggtacccgta ttcccaataa agcctcttgc tgtttgcatc    5700
cgaatcgtgg actcgctgat ccttgggagg gtctcctcag attgattgac tgcccacctc    5760
gggggtcttt cagtaggatc tcgaccgatg cccttgagag ccttcaaccc agtcagctcc    5820
ttccggtggg cgcggggcat gactatcgtc gccgcactta tgactgtctt ctttatcatg    5880
caactcgtag gacaggtgcc ggcagcgctc tgggtcattt cggcgagga ccgctttcgc    5940
tggagcgcga cgatgatcgg cctgtcgctt gcggtattcg gaatcttgca cgccctcgct    6000
caagccttcg tcactggtcc cgccaccaaa cgtttcggcg agaagcaggc cattatcgcc    6060
ggcatggcgg ccgacgcgct gggctacgtc ttgctggcgt tcgcgacgcg aggctggatg    6120
gccttcccca ttatgattct tctcgcttcc ggcggcatcg gatgcccgc gttgcaggcc    6180
atgctgtcca ggcaggtaga tgacgaccat cagggacagc ttcaaggatc gctcgcggct    6240
cttaccagcc taacttcgat cattggaccg ctgatcgtca cggcgattta tgccgcctcg    6300
gcgagcacat ggaacgggtt ggcatggatt gtaggcgcct gatgcggtat tttctcctta    6360
cgcatctgtg cggtatttca caccgcatat ggtgcactct cagtacaatc tgctctgatg    6420
ccgcatagtt aagccagccc cgacacccgc caacacccgc tgacgcgccc tgacgggctt    6480
gtctgctccc ggcatccgct tacagacaag ctgtgaccgt ctccgggagc tgcatgtgtc    6540
agaggttttc accgtcatca ccgaaacgcg cgagacgaaa gggcctcgtg atacgcctat    6600
ttttataggt taatgtcatg ataataatgg tttcttagac gtcaggtggc acttttcggg    6660
gaaatgtgcg cggaacccct atttgtttat ttttctaaat acattcaaat atgtatccgc    6720
tcatgagaca ataaccctga taaatgcttc aataatattg aaaaaggaag agtatgagta    6780
ttcaacattt ccgtgtcgcc cttattccct ttttgcggc attttgcctt cctgtttttg    6840
ctcacccaga aacgctggtg aaagtaaaag atgctgaaga tcagttgggt gcacgagtgg    6900
gttacatcga actggatctc aacagcggta agatccttga gttttcgc cccgaagaac    6960
gttttccaat gatgagcact tttaaagttc tgctatgtgg cgcggtatta tcccgtattg    7020
acgccgggca agagcaactc ggtcgccgca tacactattc tcagaatgac ttggttgagt    7080
actcaccagt cacagaaaag catcttacgg atggcatgac agtaagagaa ttatgcagtg    7140
```

-continued

```
ctgccataac catgagtgat aacactgcgg ccaacttact tctgacaacg atcggaggac      7200
cgaaggagct aaccgctttt ttgcacaaca tgggggatca tgtaactcgc cttgatcgtt      7260
gggaaccgga gctgaatgaa gccataccaa acgacgagcg tgacaccacg atgcctgtag      7320
caatggcaac aacgttgcgc aaactattaa ctggcgaact acttactcta gcttcccggc      7380
aacaattaat agactggatg gaggcggata agttgcagg accacttctg cgctcggccc       7440
ttccggctgg ctggtttatt gctgataaat ctggagccgg tgagcgtggg tctcgcggta      7500
tcattgcagc actggggcca gatggtaagc cctcccgtat cgtagttatc tacacgacgg      7560
ggagtcaggc aactatggat gaacgaaata gacagatcgc tgagataggt gcctcactga      7620
ttaagcattg gtaactgtca gaccaagttt actcatatat actttagatt gatttaaaac      7680
ttcattttta atttaaaagg atctaggtga agatccttt tgataatctc atgaccaaaa       7740
tcccttaacg tgagttttcg ttccactgag cgtcagaccc cgtagaaaag atcaaaggat      7800
cttcttgaga tcctttttt ctgcgcgtaa tctgctgctt gcaaacaaaa aaaccaccgc       7860
taccagcggt ggtttgtttg ccggatcaag agctaccaac tcttttttccg aaggtaactg     7920 gcttcagcag agcgcagata ccaaatactg tccttctagt gtagccgtag ttaggccacc     7980
acttcaagaa ctctgtagca ccgcctacat acctcgctct gctaatcctg ttaccagtgg     8040
ctgctgccag tggcgataag tcgtgtctta ccgggttgga ctcaagacga tagttaccgg     8100
ataaggcgca gcggtcgggc tgaacggggg gttcgtgcac acagcccagc ttggagcgaa     8160
cgacctacac cgaactgaga tacctacagc gtgagcattg agaaagcgcc acgcttcccg     8220
aagggagaaa ggcggacagg tatccggtaa gcggcagggt cggaacagga gagcgcacga     8280
gggagcttcc agggggaaac gcctggtatc tttatagtcc tgtcgggttt cgccacctct     8340
gacttgagcg tcgatttttg tgatgctcgt caggggggcg gagcctatgg aaaaacgcca     8400
gcaacgcggc cttttttacgg ttcctggcct tttgctggcc ttttgctcac atgttctttc    8460
ctgcgttatc ccctgattct gtggataacc gtattaccgc ctttgagtga gctgataccg     8520
ctcgccgcag ccgaacgacc gagcgcagcg agtcagtgag cgaggaagcg gaagagcgcc     8580
caatacgcaa accgcctctc cccgcgcgtt ggccgattca ttaatgcagg                8630
```

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: PCR primer
<220> FEATURE:
<221> NAME/KEY: misc_feature
<222> LOCATION: (1)..(28)
<223> OTHER INFORMATION: delta gag+

<400> SEQUENCE: 3
gtgccggcat ctaatgtttg cgcctgcg                                         28

<210> SEQ ID NO 4
<211> LENGTH: 46
<212> TYPE: DNA
<213> ORGANISM: Artificial Sequence
<220> FEATURE:
<223> OTHER INFORMATION: Description of Artificial Sequence: PCR primer
<220> FEATURE:
<221> NAME/KEY: misc_feature
<222> LOCATION: (1)..(46)
<223> OTHER INFORMATION: delta gag/Not-

```
-continued

<400> SEQUENCE: 4
atagtttagc ggccgctaat tttcagacaa atacagaaac acagtc                    46

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: PCR primer
<220> FEATURE:
<221> NAME/KEY: misc_feature
<222> LOCATION: (1)..(42)
<223> OTHER INFORMATION: delta gag/Xho-

<400> SEQUENCE: 5
gtccgctcga gctaattttc agacaaatac agaaacacag tc                        42

<210> SEQ ID NO 6
<211> LENGTH: 47
<212> TYPE: DNA
<213> ORGANISM: Artificial Sequence
<220> FEATURE:
<223> OTHER INFORMATION: Description of Artificial Sequence: annealing
      oligonucleotide
<220> FEATURE:
<221> NAME/KEY: misc_feature
<222> LOCATION: (1)..(47)
<223> OTHER INFORMATION: SA-oligo(+)

<400> SEQUENCE: 6
tcgacaaagt taagtaatag tccctctctc caagctcact tacaggc                   47

<210> SEQ ID NO 7
<211> LENGTH: 47
<212> TYPE: DNA
<213> ORGANISM: Artificial Sequence
<220> FEATURE:
<223> OTHER INFORMATION: Description of Artificial Sequence: annealing
      oligonucleotide
<220> FEATURE:
<221> NAME/KEY: misc_feature
<222> LOCATION: (1)..(47)
<223> OTHER INFORMATION: SA-oligo(-)

<400> SEQUENCE: 7
ggccgcctgt aagtgagctt ggagagaggg actattactt aactttg                   47

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: PCR primer
<220> FEATURE:
<221> NAME/KEY: misc_feature
<222> LOCATION: (1)..(28)
<223> OTHER INFORMATION: MUT/Leader-ATG/+

<400> SEQUENCE: 8
gtgccggcat ctagtgtttg cgcctgcg                                        28

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: PCR primer
<220> FEATURE:
<221> NAME/KEY: misc_feature
```

<222> LOCATION: (1)..(28)
<223> OTHER INFORMATION: MUT/Leader-ATG/-

<400> SEQUENCE: 9
cgcaggcgca aacactagat gccggcac                                              28

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: PCR primer
<220> FEATURE:
<221> NAME/KEY: misc_feature
<222> LOCATION: (1)..(30)
<223> OTHER INFORMATION: SD1+

<400> SEQUENCE: 10
gaagacatga ccagatatgc ctattattac                                            30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: PCR primer
<220> FEATURE:
<221> NAME/KEY: misc_feature
<222> LOCATION: (1)..(30)
<223> OTHER INFORMATION: SD1-

<400> SEQUENCE: 11
gtaataatag gcatatctgg tcatgtcttc                                            30

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: PCR primer
<220> FEATURE:
<221> NAME/KEY: misc_feature
<222> LOCATION: (1)..(29)
<223> OTHER INFORMATION: SA1+

<400> SEQUENCE: 12 cattttcct tcaaggtttc acatttggc                                              29

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: PCR primer
<220> FEATURE:
<221> NAME/KEY: misc_feature
<222> LOCATION: (1)..(29)
<223> OTHER INFORMATION: SA1-

<400> SEQUENCE: 13
gccaaatgtg aaaccttgaa ggaaaaatg                                             29

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: PCR primer
<220> FEATURE:

-continued

```
<221> NAME/KEY: misc_feature
<222> LOCATION: (1)..(30)
<223> OTHER INFORMATION: AATAAA+

<400> SEQUENCE: 14
gatggcaaag aaattaagcg actgaatgtt                                          30

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: PCR primer
<220> FEATURE:
<221> NAME/KEY: misc_feature
<222> LOCATION: (1)..(31)
<223> OTHER INFORMATION: AATAAA-

<400> SEQUENCE: 15
gaacattcag tcgcttaatt tctttgccat c                                        31

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: PCR primer
<220> FEATURE:
<221> NAME/KEY: misc_feature
<222> LOCATION: (1)..(36)
<223> OTHER INFORMATION: eGFP+

<400> SEQUENCE: 16
gcggccgcca tggtgagcaa gggcgaggag ctgttc                                   36

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence: PCR primer
<220> FEATURE:
<221> NAME/KEY: misc_feature
<222> LOCATION: (1)..(34)
<223> OTHER INFORMATION: eGFP-

<400> SEQUENCE: 17
ctcgagttat cgagatctga gtccggactt gtac                                     34
```

RETROVIRAL GENE TRANSFER VECTORS

The invention relates to novel retroviral gene transfer vectors, preferably expression vectors, which, because of a reduced content of viral genes, are distinguished by a higher safety standard and expression of non-viral nucleotide sequences in higher amounts.

The expression of foreign proteins in pro- and eukaryotic cells, i.e. of proteins which are usually expressed only in very small amounts, or not at all, in these cells, plays an essential role in research into the function of proteins, production of proteins and treatment of diseases. A prerequisite for expression of a foreign gene is that the genetic material which codes for the protein is introduced into the target cell. This is as a rule achieved with the aid of so-called vectors. Vectors are DNA molecules into which the DNA which codes for the protein to be expressed has been cloned and which contain DNA sequences which are of importance for expression of the protein.

For stable gene transfer into mammalian cells, retroviral vectors based on mouse leukaemia viruses (MLV) are currently the most frequently used and best characterized system (Miller, A. D. (1993) Methods Enzymol, 217; 581–599). Fields of use of retroviral vectors are, for example, over-expression of proteins with the aim of obtaining pure proteins, expression cloning with the aim of identifying new proteins, and stable expression of a protein in a body cell with the aim of a therapeutic action of the expressed protein. The level of transgene expression in the cell system relevant to the disease is decisive for the therapeutic potential of gene transfer here. For clinical use of gene transfer vectors, the safety of the vectors is furthermore of decisive importance. On the one hand, expression of viral gene products must be excluded here, since these may display a pathogenic action in the body. On the other hand, recombination with naturally occurring viruses should be ruled out, to prevent viral proteins being expressed under the control of the regulatory element introduced into the vector, or novel viruses with unknown properties being formed.

Retroviral vectors can exist in two forms, as proviral DNA or as vector RNA. Proviral double-stranded DNA is integrated in a stable manner in the genome of the target cell. From this, the so-called genomic vector transcript is read, which is built up like a cell mRNA (messenger RNA), and is packed in viral particles and transmits the genetic information of the retrovirus. After retroviral infection of a target cell, the genomic vector transcript is transcribed by reverse transcription into a new provirus and integrated in a stable manner into the genome of the cell (Miller, A. D. (1993) Methods Enzymol. 217: 581–599).

The provirus is flanked at the 5'- and at the 3'-end by "long terminal repeats" (LTR), which include the regions U3, R and U5 (FIG. 1). The U3 region contains enhancer/promoter sequences which control transcription of the vector. The R region carries the polyadenylation signal. The U5 region contains sequences which are necessary for integration of the retrovirus. The coding sequences of the exogenous protein are usually between 5'- and 3'-LTR in the vector and are flanked by control sequences of regulatory importance which are essential for the progress of the retroviral life cycle and at the same time influence the half-life of the RNA and the translation efficiency of the exogenous protein. The transcription start of the RNA lies at the boundary of the R region of the 5'-LTR. The transcription end is determined by polyadenylation and termination signals in the R region of the 3'-LTR. A polyadenosine tail is attached at the end of the R region of the 3'-LTR. Splicing signals of the retrovirus/vector can lead to transcripts with internal deletions.

The 5'-untranslated region of the retroviral vector is composed of (A. D. Miller (1993) loc. cit.):

R region and U5 region of the 5'-LTR (approx. 150 nucleotides, necessary for reverse transcription and integration)

Primer binding site (18 nucleotides, necessary for reverse transcription)

Leader region (in current retroviral vectors at least 800 nucleotides long). This follows the primer binding site and extends to the start of the coding sequence. The leader region contains the packing and dimerization signal, which is necessary for incorporation of the RNA into retroviral particles. At the start of the leader lies the retroviral splicing donor, and at the end of the leader there can be a cryptic (i.e. recognized only in a portion of the transcripts) splicing acceptor. The splicing donor and splicing acceptor determine the start and end of the RNA sequences which can be removed from the primary transcript by the splicing operation even before export into the cytoplasm. The efficiency of the splicing reaction depends on the suitability of the splicing signals. In addition to the sequences of the splicing donor and splicing acceptor, the polypyrimidine tract lying before the splicing acceptor and the subsequent so-called branch site (see below) determine the efficiency of the splicing (Zhuang, Y. A. et al. (1989) Proc. Natl. Acad. Sci. USA, 86: 2752–2756).

The efficiency of the translation is impaired by the long length of the 5'-untranslated region (5'-UTR). The splicing signals of the leader can give rise to shortened transcripts with significantly shorter 5'-UTR, which have an increased translation efficiency (Armentano, D. et al. (1987) J. Virol. 61: 1647-1620; Bender, M. A. et al. (1987) J. Virol. 61: 1639–1646; Krall, W. J. et al. (1996) Gene Ther. 3: 37–48).

The 3'-untranslated region of the RNA contains the polypurine tract, which is necessary for the reverse transcription, and the U3 and R region of the 3'-LTR.

After the retroviral life cycle, the U3 region of the 3'-UTR is copied into both LTRs. If the U3 region contains enhancer/promoter regions, these control the transcription of the vector-RNA in the infected cell (Baum, C. et al. (1995) J. Virol. 69: 7541–7547). The end of the RNA is the polyadenosine tail of approx. 200 nucleotides, which co-determines the stability in the cytoplasm.

In addition to the control elements, retroviruses contain nucleotide sequences which code for viral proteins. These include the gag gene, which codes for structure proteins of the virus, the pro gene, which codes for the virion protease, the pol gene, which codes for the reverse transcriptase, and the env gene, which codes for virus envelope glycoproteins. If the retroviral vector does not contain one of these genes, it is replication-incompetent. To produce infectious virus particles from a replication-incompetent retroviral vector, a helper virus and/or a packing-competent cell line which provide the properties lacking from the retroviral vector are required.

The viral sequences contained in the retroviral vectors can give rise to recombination with complementary retroviruses in the packing cell, as a result of which replication-competent retroviruses, which can induce leukaemias and encephalopathies in animal studies, can form (Anderson, W. F. (1993) Hum. Gene Ther. 4; 311–321; Munk, C. (1997) PNAS 94: 5837–5842). The residual gag and pol genes furthermore contain a large number of cryptic reading frames, i.e. nucleotide sequences which code for an amino acid sequence in a reading frame other than for the actual gene, but in the normal case are not read, since the control elements and/or the start codon are missing. Nevertheless, it cannot be ruled out that immunogenic or toxic peptides can be generated in the target cell by the open reading frame.

The target cell of the retroviral expression vector is transduced with infectious virus particles. These particles are produced with the aid of a packing-competent cell line. It is important here that as many infectious virus particles as possible per ml of cell culture supernatant are produced by the packing-competent cells, that is to say that the virus titre, stated in infectious units per ml of culture medium, is as high as possible.

Retroviral vectors are often produced on the basis of control elements which are taken from mouse laukaemia viruses (MLV) (Miller, A. D., loc. cit.). These vectors are called MLV-based vectors. A central field of use of this group of retroviral vectors is gene transfer in haematopoietic stem cells (Dunbar, C. E. (1996) Ann. Rev. Med. 47: 11–20). Therapeutic actions are said to be achieved here with the by transfer and expression of the protein coded by the vector. The protein is produced permanently in the cells. Long-lasting treatment which acts directly on the genetic defects on which the disease is based is therefore conceivable. For example, the vector can carry genes such as human mdr1 (multidrug resistance 1) to protect the stem cells against the toxic side effects of a cytostatic drug treatment (stem cell protection) (Baum, C. et al, (1996) Gene Ther. 3: 1–3, Baum, C. et al, (1995) loc. cit.).

The prior art describes retroviral vectors in which the gag gene including a 60 bp sequence of the 5'-UTR lying directly 5' (i.e. upstream) of the start codon of the gag gene has been removed. However, only very low virus titres have been obtained with these vectors. Works by Armentano and Bender from 1987 (Armentano, D. et al. (1987) J. Virol. 61: 1647–1650); Bender, M. A. et al. (1987) J. Virol. 61: 1639–1646) have shown that the virus titre of retroviral vectors derived from MLV is higher if some of the gag gone (at least 400 bp) is left in the vector. It is concluded from this that the packing signal decisive for the retroviral titre is not limited only to the 5'-untranslated region of the retrovirus, but extends into the viral gag sequence. This opinion has since also been expressed in textbooks (Kriegler, M. (1990) Gene Transfer and Expression, Stockton Press, New York, p. 52). Por this reason, no retroviral vectors which contain fewer than 400 bp of the gag gene or in which the gag sequences have been removed completely are produced in the prior art. The vectors corresponding to the prior art are also called (gag+) vectors.

In retroviruses, the translation level of retroviral sequences depends on the presence of appropriate splicing signals and the position of the start codon in the spliced RNA. A splicing signal is understood as a nucleotide sequence which regulates splicing of the RNA formed during the transcription. These splicing signals consist of different nucleotide sequences, depending on the virus strain on which the vector is based. However, a splicing signal originating from a certain virus is as a rule also active in vectors which are derived from other viruses (Bowtell, D. D. et al. (1988) J. Virol. 62: 2464–2473). All splicing signals have a common consensus sequence which contains a "branch site". The nucleophile which is necessary for the first transesterification step of the splicing reaction is designated the "branch site". An denosine nucleotide usually functions as the "branch site". In viruses derived from MLV, the translation level of retroviral env sequences depends on the presence of appropriate splicing signals and the position of the start codon in the spliced RNA, This observation was the basis of the development of MFG vectors (Riviere, I. et al. (1995) PNAS 92: 6733–6737). The abbreviation MFG is derived from a proper name which is not explained in the literature (Dranoff, G. et al. (1993) Proc. Natl. Acad. Sci. USA 90: 3539–3543). MFG vectors are built up as (gag+) vectors and additionally also contain a fragment of the retroviral pol gene which carries the Moloney MLV splicing acceptor. The coding sequence of the gene to be transferred is placed exactly at the site and as a substitute of the retroviral env gene (FIG. 1). Compared with other MLV vectors with identical enhancer-promoter sequences, MFG vectors show an increased expression of the exogenous gene (Krall, W. J. et al. (1996) Gene Ther. 3: 37–48). However, not more than 50% of the transcripts produced are spliced in MFG vectors, so that a high proportion of the transcripts is still lost for the translation. MFG vectors also show problems in respect of the safety aspect, since they carry high proportions of the viral gag and pol genes to achieve a high packing efficiency and good splicing rates. These viral sequences can give rise to recombination with complementary retroviruses in the packing cell (see above). MFG vectors are therefore of only limited suitability for experimental use and not very suitable for therapeutic use, since they carry safety risks which are too high because of the immunogenic or toxic potential.

Another group of MLV-based retroviral vectors are the LX vectors. LX vectors Are also (gag+) vectors. LX means LTR gene x (Miller, A. D. and G. J. Rosman (1987) Biotechniques 7: 980–990). In LX vectors, the transgene is incorporated centrally into the gag region (approx. 400 base pairs 3' of the gag start codon, which has been mutated to a stop codon). The other gag, pol and env sequences have been removed completely. The LX vectors thus carry fewer viral sequences than the MFG vectors. Nevertheless, the efficiency of the splicing—and therefore also of the translation of the transgene—with the LX vectors is as a rule lower than with the MFG vectors (Armentano, D. et al. (1987) J. Virol. 61: 1647–1620; Bender, M. A. et al. (1987) J. Virol. 61: 1639–1646; Krall, W. J. et al. (1996) Gene Ther. 3: 37–48).

LX or MFG vectors which, in addition to the nucleotide sequences which code for the exogenous proteins, also contain sequences for residual viral gene products and at least 400 bp of the gag gene have hitherto found use in the prior art. As already mentioned, this results in the disadvantage that with these vectors there is always the risk that viral proteins or peptides are also expressed and recombination with other viruses takes place. Furthermore, the minimum of 400 bp of the gag gene reduce the cloning capacity, i.e. the maximum length of the exogenous nucleotide sequence of the vector, since a retroviral vector can comprise not more than 10 kb. Another disadvantage of MFG or LX vectors lies in the fact that at least half the transcripts are not spliced and are therefore not available for translation.

An object of the present invention is therefore to provide retroviral vectors which do not have the disadvantages mentioned for the vectors used in the prior art. In particular, it is an object of the present invention to provide vectors which meet a higher safety standard than the vectors known to date. In particular, the risk of viral proteins being generated in the target cells should be minimized; preferably, no immunogenic or toxic proteins should be expressed. An essential aim is to reduce or rule out completely the probability of recombination with other viruses. It is furthermore an object of the invention to provide retroviral expression vectors which have a comparable virus titre and a higher cloning capacity with respect to the vectors used in the prior art and allow expression of non-viral nucleotide sequences in large amounts.

According to the invention, the object is achieved in that for the first time retroviral vectors which contain less than 400 bp of the nucleotide sequence which codes for gag are provided. The vectors according to the invention preferably contain less than 200 bp or less than 80 bp of a nucleotide sequence which codes for gag. According to a preferred embodiment of the present invention, the retroviral vectors contain no sequences or sequence sections which code for gag. Vectors in which the sequences which code for viral proteins are removed completely are particularly preferred. The retroviral vector is preferably used as an expression vector.

The invention thus relates to a retroviral vector which contains a nucleotide sequence N of the general formula 5'-end-[5'-UTR]-[gag]-[ex]-[vir]-3'-end wherein

[5'-UTR] represents a non-coding nucleotide sequence which lies in retroviruses directly 5', i.e. upstream, of the start codon of the gag gene,

[gag] represents a section of the nucleotide sequence which codes for the gag gene,

[ex] represents a non-viral nucleotide sequence and

[vir] represents a retroviral nucleotide sequence, and which is characterized in that the number of nucleotides in [gag] is less than 400 bp.

In the context of the present invention, it has been found, surprisingly, that in contrast to prevailing opinion, high virus titres can he achieved with the construction according to the invention, which contains less than 400 bp of the gag gene and according to a particularly preferred embodiment no nucleotides which code for the gag gene, and a high expression of the non-viral nucleotide sequences is possible. By reducing the gag content, the cloning capacity and the safety of the vectors according to the invention are increased.

Possible [5'-UTR] are all nucleotide sequences which, in retroviruses or retroviral constructions derived from retroviruses, lie directly 5', i.e. upstream, of the start codon of the gag gene, where, in the retroviral constructions, these nucleotide sequences should not be changed such that the change leads to a significant (more than one order of magnitude) reduction in the virus titre or translation efficiency compared with the non-changed sequence. Mutations and relatively small deletions which do not lead to a reduction in the virus titre or translation efficiency are included according to the invention. A deletion of a sequence section comprising at least 60 bp which lies directly before the start codon of the gag gene is excluded according to the invention. According to the invention, "directly before the start codon" means that apart from incorporated splicing acceptor nucleotides and/or polylinker fragments, there are no further nucleotides between this sequence section and the start codon of the gag gene.

According to a particular embodiment of the invention, the [5'-UTR] contains at least one sequence section which represents a splicing acceptor. The splicing acceptor can originate from the FMEV vector SF1MSN, but also from other retroviral or non-retroviral vectors, viruses such as, for example, HIV, or also from intron-containing eukaryotic genes. The splicing acceptor here can be a large genomic restriction fragment of the viral pol gene. A synthetically produced oligonucleotide which represents only the minimum consensus for the splicing acceptor (including the so-called branch site) and has a length of 10–100, preferably 10–50, particularly preferably 20–50 base pairs is particularly preferred.

In another preferred embodiment, [5'-UTR] contains at no site the nucleotide triplet AUG (adenine-uracil-guanine), which serves as the start codon in retroviruses. As a result, translation of cryptic open reading frames in [5'-UTR] is ruled out. This also leads to an increase in the safety standard. The AUG-deleted nucleotide sequences are obtainable, for example, by a mutation by means of "site-directed mutagenesis" (see example 4).

According to the invention, 5'-UTR can contain a leader sequence. According to a particular embodiment, this can originate from the MESV virus (Grez, M. et al., Proc. Natl. Acad. Sci. USA 87: 9202–9206 (1990)), but it is also conceivable to use the leader sequence of MoMoLV or MoMuSV (Miller, A. D. and Rosmann, G. J., loc. cit.). The viruses of which the 5'-leaders can be used in the retroviral vector according to the invention furthermore include, for example, "spleen necrosis virus" (Olson P. et al. (1994) J. Virol. 68: 7060–7066) or "Harvey murine sarcoma virus" (Berlioz, C. et al. (1995) J. Virol. 69: 6400–6407), but are not limited to these.

The sequence element [gag] can be taken from any desired sections of the nucleotide sequence which codes for the gag protein. According to the invention, [gag] contains less than 400 bp. Preferably, [gag] contains less than 200 bp, preferably less than 80 bp.

According to a particularly preferred embodiment of the invention, the retroviral expression vector 5' of [ex] contains no nucleotides or sequence fragments which originate from the gag gene. This means that the non-viral nucleotide sequence [ex] lies directly 3' of [5'-UTR]. According to the invention, "directly 3' of [5'-UTR]" means that apart from incorporated splicing acceptor nucleotides and/or polylinker fragments, there are no further nucleotides between this sequence section and the first nucleotide of [ex]. The non-viral nucleotide sequence [ex] is then incorporated at the site of the gag gene into the retroviral expression vector. As a result, the architecture of a native retrovirus is reconstructed. This accurate imitation of the structure of the native retrovirus leads to an increased expression of the gene, which can be increased further by introducing a synthetic splicing acceptor.

This particularly preferred embodiment, in which [ex] replaces the gag gene, can be obtained by removing the residual gag contents by means of PCR (see example 1). These techniques are known to the expert (Ausubel, I. et al. (1994) Current Protocols in Molecular Biology. John Wiley & Sons, New York). This leads to a vector which carries a "multiple cloning site" instead of the gag gene. A multiple cloning site is a nucleotide sequence which contains various cutting sites for restriction enzymes. The desired non-viral nucleotide sequence [ex] can then be cloned directly on the 3'-end of the [5' region] by means of techniques known to the expert.

According to the invention, the nucleotide sequence [ex] is between [gag] and [vir] and represents a non-viral nucleotide sequence. Preferably, it contains at least one nucleotide sequence which codes for a non-viral protein. The sequence [ex] can also comprise a non-viral RNA sequence. According to one embodiment of the invention, the non-viral nucleotide sequence [ex] contains a nucleotide sequence which codes for the MDR1 gene. According to another embodiment, [ex] contains a nucleotide sequence which codes for enhanced humanized green fluorescent protein, which is suitable as a cytoplasmic marker (EGFP; Cormack, B. P. et al. (1996) Gene 173: 33–38).

Other sequences which are suitable according to the invention include, but without being limited to the examples mentioned:

genes which, like EGFP, are used as cell markers (e.g. surface proteins such as human low affinity nerve growth factor receptor (Fehse, B. et al. (1997) Hum. Gene Ther. 8: 1815–1824))

genes which, like MDR1, can impart resistance to cytotoxic drugs (e.g. dehydrofolate reductase; Zhao, S. C. et al. (1997) Hum. Gene Ther. 8: 903–909).

genes which can correct congenital metabolic diseases (e.g. a-L-iduronidase for treatment of Hurler-Scheie syndrome; Huang, M. M. et al. (1997) Gene Ther. 4: 1150–1159).

Since the nature of the gene has no influence on the improvement according to the invention of the vectors, potentially all sequences which are transferred into retroviral vectors are of interest as [ex]. In the preferred embodiment of the invention, the cloning capacity for the genes to be transferred is increased by approx. 400 base pairs by elimination of all virus-coding sequences.

The nucleotide sequences which code for non-viral proteins can be cloned into the non-viral nucleotide sequence [ex] either in the reading direction, i.e. in the 5'→3' direction, or in the opposite orientation, i.e. in the 3'→5' direction. According to a particular embodiment, the first nucleotide of the start codon of the nucleotide sequence which codes for the non-viral protein represents the 5'-end of [ex]. In addition to the region which codes for proteins, the non-viral nucleotide sequence [ex] can furthermore comprise regulatory nucleotide sequences. If the nucleotide sequence [ex] contains several nucleotide sequences which code for non-viral proteins, these nucleotide sequences can either follow one another directly or be separated from one another by regulatory nucleotide sequences. According to the invention, regulatory nucleotide sequences here are to be understood as meaning all nucleotide sequences which can influence the expression of the non-viral proteins. These include, in particular, splicing acceptor sites. Further possibilities for linking transcription units in [ex] are internal ribosome entry signals, internal promoters or fusion genes (Hildinger, M. et al. (1998) Hum. Gene Ther. 9: 33–42).

Important regulatory nucleotide sequences are furthermore promoter and enhancer sequences. The promoter and enhancer sequences can originate from any desired viral or non-viral genes. The promoters preferably originate from MLV (Baum, C. et al. (1995) J. Virol. 69: 7541–7547), but are not limited to this. Promoter and enhancer sequences which are specific for the particular target cell are particularly suitable because a cell-specific expression is possible in this way.

The promoter and enhancer sequences can lie both at the 5'-end and at the 3'-end of [ex]. They can likewise lie at any position in [ex], including within the nucleotide sequences which code for non-viral proteins.

According to another embodiment of the invention, the nucleotide sequences which code for non-viral proteins contain those mutations which, without changing the protein sequence coded by the non-viral nucleotide sequence, lead to removal of cryptic splicing sites and/or cryptic poly-A sites. This avoids the mRNAs formed by transcription of the non-viral nucleotide sequences which code for the proteins being incorrectly spliced or too short if the poly-A tail is attached too early (McIvor, R. S. (1990) Virology 176: 652–655; Johnson, J. J. et al. (1995) Hum. Gene Ther. 6: 611–623). Site-directed mutagenesis is the currently customary technique preferred by the expert for introduction of mutations. According to the invention, however, other techniques can also be used. Other mutations which are of interest according to the invention comprise removal of ATG triplets, which can lead to a defective start to the translation of the sequence in [ex], improvement of the translation start of the sequence in [ex] by optimization of the so-called Kozak consensus sequence (Krall, W. J. et al. (1996) Gene Ther. 3: 37–48), or introduction of signals which lead to an improved nucleus export of the RNA (Pasquinelli, A. E. et al. (1997) EMBO J. 16: 7500–7510); the latter can also be incorporated into the vector at a site other than in [ex].

According to the invention, [vir] represents a retroviral sequence which can contain nucleotide sequences which code for one or more viral proteins or for parts thereof. In the context of the present invention, the sequence sections which code for viral proteins are preferably reduced in number and length in the retroviral vector. In particular, the vector preferably contains no sequences or sequence sections which code for the pol protein, the pro protein, the env protein and/or other viral proteins.

According to the invention, an expression vector which contains no nucleotide sequences which code for the gag protein, particularly preferably none which code for the gag protein or for other viral proteins, is preferred. This means that the retroviral vector overall contains no nucleotide sequences which code for residual viral proteins. A retroviral expression vector which both contains no sequence sections which code for residual viral proteins or for parts thereof and contains the nucleotide triplet AUG at no site apart from in [ex] is especially preferred. This ensures that both no residual viral proteins or parts thereof and no cryptic peptides are produced. The exclusion of nucleotide sequences which code for viral proteins ensures that the risk of recombination, based on sequence homology, with MLV sequences in the packing cell is minimized. The risk of an aberrant translation of viral peptides in the target cell is also reduced. Furthermore, the safety standard is increased in that the retroviral vector contains no start codon with the sequence AUG.

Downstream of the nucleotide sequence N, i.e. 3', is in general a 3'-LTR in the vectors according to the invention. According to a particular embodiment, the 3'-LTR from spleen focus forming virus (SFFVp) can be used. The viruses of which the 3'-LTR can be used furthermore include other MLV, such as Friend-MLV, MPSV or MOMLV (Baum, C. et al. (1995) j. Virol. 69: 7541–7547), but are not limited to these.

According to a particularly preferred embodiment, the retroviral vectors according to the invention are the vectors SFβ71m4 (DSM 12066) and SFβ91 mSA1 (DSM 12065), deposited on Mar. 20, 1998, under conditions of the Budapest Treaty at the Deutsche Sammlung von Mikroorganismen und Zelikulturen [German Collection of Microorganisms and Cell Cultures], Mascheroder Weg 1b, 38124 Braunschweig, or vectors derived therefrom.

The vector deposited under DSM 12065 is distinguished in that all the nucleotide sequences which code for viral proteins have been removed. At the 5'-end of the proviral DNA are the U3, R and U5 regions of the 5'-LTR. The CAP site at which the transcription of the viral mRNA starts lies in the 5'-LTR. 3' of 5'-LTR lies a nucleotide sequence which contains a splicing acceptor (SA), a packing region (Ψ) and a splicing donor (SD). Nucleotide 271 (counted from the CAP site) has been mutated to remove a cryptic AUG. At the site at which the sequences which code for the gag gene were to be found is the variant mSA1 of the MDR1 gene, which is distinguished in that a cryptic splicing acceptor has been mutated at position 2320 (counted from the start codon of the MDR1 gene). 3' of the MDR1 variant mSA1 is the 3'-LTR with the U3, R and U5 regions (cf. FIG. 2).

The vector deposited under DSM 12066 is distinguished in that all the nucleotide sequences which code for viral proteins have been removed. At the 5'-end of the proviral DNA are the U3, R and U5 regions of the 5'-LTR. The CAP site at which transcription of the viral RNA starts lies in the 5'-LTR. 3' of the 5'-LTR lies a nucleotide sequence which contains a splicing acceptor (SA), a packing region (Ψ) and a splicing donor (SD). At the site at which the sequences which code for the gag gene were to be found is the variant m4 of the MDR1 gene, which is distinguished in that a cryptic splicing donor has been mutated at position 339 (counted from the start codon of the MDR1 gene), a cryptic splicing acceptor has been mutated at position 2320 and a cryptic poly(A) signal has been mutated at position 3303. 3' of the MDR1 variant m4 is the 3'-LTR with the U3, R and U5 regions (cf. FIG. 2).

According to the invention, a vector which is derived from the vector deposited under DSM 12066 and in which a cryptic AUG has additionally been mutated at position 271 (counted from the CAP site) is furthermore preferred.

The last three vectors mentioned, i.e. the vectors deposited under DSM 12065 and 12066 and the vector derived from DSM 12066, are particularly preferably suitable for transfection of haematopoietic stem cells in the context of gene therapy in order to achieve resistance of the haematopoietic stem cells during chemotherapy (see below).

The present invention furthermore relates to a process for the preparation of an infectious virus particle. The techniques on which the process is based are known to the expert (Ausubel, I. et al. (1994) Current Protocols in Molecular Biology, John Wiley & Sons, New York). With the aid of a packing-competent cell line and/or a helper virus, infectious virus particles which contain the retroviral vector according to the invention are prepared. The helper virus is produced by the packing cells as a replication-competent particle.

The genome of the helper virus has been changed by genetic engineering so that the RNA of the helper virus which codes for the virus protein cannot be packed into the virus particles (Miller, A. D. et al. (1993) Methods Enzymol. 217: 581–599).

The present invention furthermore relates to a host cell transfected with the retroviral vector according to the invention. The host cell is preferably infected with an infectious virus particle (see above) which contains the retroviral vector according to the invention. This host cell can be chosen from the available immortalized haematopoietic cell lines (Baum, C. et al. (1995) J. Virol. 69: 7541–7547) or primary human blood cells (Eckert, H. G. et al. (1996) Blood 88: 3407–3415), but is not limited to these. Preferably, the host cell is a K-562 cell (human erythroleukaemia cell; Lozzio, C. B. et al. (1976) Cancer Res. 36: 4657–4662), which is transfected with the vector SFβ71m4 (DSM deposit number DSM 12066) or with the vector SFβ91mSA1 (DSM deposit number DSM 12065).

The invention furthermore relates to a process for the preparation of proteins, in which a host cell which has been transfected with a retroviral vector according to the invention or a virus particle according to the invention is cultured in a suitable medium under conditions which are necessary for expression of the retroviral proteins for which the nucleotide sequences in the nucleotide sequence [ex] code. These conditions can include culture in standard cell culture media, such as Delbecco's modified essential medium (DMEM), which are supplemented with animal serum (for example foetal calf serum) (Ausubel et al., loc. cit.). Thereafter, the protein produced is purified with the aid of techniques known to the expert (Ausubel et al., loc. cit.), by separating it off from the cells and the medium.

According to the invention, the retroviral vector can be used therapeutically. This means that it is a constituent of a pharmaceutical preparation which additionally comprises pharmaceutically tolerated auxiliaries and/or excipients.

According to a particular embodiment of the invention, the retroviral gene transfer or expression vector is used in gene therapy. This includes the vector being present in a pharmaceutical preparation such that it can be introduced into the target cell. The retroviral vector according to the invention is preferably present packed in an infectious virus particle. The retroviral vector is preferably used for transfection of haematopoietic stem cells (Baum, C. et al. (1997) in: Concepts in Gene Therapy (M. Strauss, W. Barranger, eds.), De Gruyter, Berlin, p. 233–266).

The retroviral vector according to the invention is furthermore used for expression cloning of genes. For this, a cDNA library which contains the gene sought is cloned into the retroviral expression vector according to the invention. After packing of the vector in infectious particles and infection of host cells with the particles, the host cell which expresses the protein sought and therefore contains the gene sought can be detected, for example by means of antibodies or via functional tests.

According to the invention, the retroviral vector can furthermore be used for expression and/or over-expression of proteins or of RNA. For this purpose, the gene to be expressed or the RNA is cloned into the retroviral vector according to the invention. After packing in infectious virus particles and infection of a suitable host cell with the particles, the desired protein can be produced by known processes.

The invention is explained below with the aid of examples, figures and sequence protocols.

EXAMPLE 1

Cloning of a Gag-Deleted Retroviral Expression Vector

The vector SFβ1 PSNEBH, which belongs to the family of FMEV vectors, was used as the basis for the clonings (PCT/EP 95/03175).

The residual gag contents of SFβ1 PSNEBH were first removed via PCR cloning strategies. For this purpose, a PCR with the primers ΔGAG+ (SEQ ID NO: 3) and AGAG/Not– (SEQ ID NO: 4) was carried out as follows:
Reaction mixture:
10 ng SFβ1 PSNEBH
50 pmol primer ΔGAG+
50 pmol primer ΔGAG/Not–
80 pmol/1 dNTP
10 µl 10× Pfu-PCR buffer
1 µl recombinant Pfu-DNA polymerase
(Stratagene GmbH, Heidelberg)
ad 100 µl H$_2$O The reaction mixture was first incubated at 95° C. for 5 min. 30 cycles were then carried out under the following conditions:
95° C. 30 s
55° C. 40 s
72° C. 2 min The reaction mixture was then incubated at 72° C. for 10 min.

The product formed (ΔGAGNOT) was phosphorylated by means of adenosine triphosphate (see Ausubel et al. 1994, loc. cit.) and subcloned into the dephosphorylated plasmid Bluescript pKS(+) digested with EcoRV (see Ausubel et al. 1994, loc. cit.). The BglII/NotI fragment of ΔGAGNOT was then cut out of the cloning vector via BglII and NotI and inserted into the SFβ1 PSNEBH opened via BglII and NotI.

This resulted in the base vector SFβ11 NEBH, which carries a multiple cloning site instead of the transgene of choice.

EXAMPLE 2

Cloning of a Splicing Acceptor Signal in SFβ11

The sequence of the splicing acceptor signal was taken from the FMEV vector SF1MSN (M. Hildinger et al. (1998) Hum. Gene Ther., 9: 33–42), the consensus sequence of the so-called branch site being modified slightly.

2 complementary oligonucleotides were synthesized, flanked by an SalI (5') and NotI (3') cutting site, with the following sequences:
SA-Oligo(+): SEQ ID NO: 6
SA-Oligo(−): SEQ ID NO: 7

Annealing of the two oligonucleotides was carried out under the following conditions (see Ausubel et al. 1994, loc. cit.):
Reaction Batch
  20 μl SA-Oligo(+) (50 pmol/μl)
  20 μl SA-Oligo(−) (50 pmol/μl)
  2.5 μl 4 mol/l NaCl
  ad 100 μl TE (10 mM Tris•HCl, 1 mM EDTDA) (pH 8.0)
This batch was incubated for 10 min at 95° C. and then cooled slowly to room temperature.

To prepare the leader fragment, a PCR with the primers ΔGAG+ (SEQ ID NO: 3) and ΔGAG/Xho− (SEQ ID NO: 5) was carried out as follows:
Reaction Mixture
  10 ng SFβ1 PSNEBH
  50 pmol primer ΔGAG+
  50 pmol primer ΔGAG/Xho−
  80 pmol/l dNTP
  10 μl 10× Pfu-PCR buffer
  1 μl recombinant Pfu-DNA polymerase (Stratagene GmbH, Heidelberg)
  100 μl H₂O The reaction mixture was first incubated at 95° C. for 5 min. 30 cycles were then carried out under the following conditions:
9° C. 30 S
2° C. 40 s
2° C. 2 min The reaction mixture was then incubated at 72° C. for 10 min.

The product formed (ΔGAGXHO) was phosphorylated by means of adenosine triphosphate (see Ausubel et al. 1994, loc. cit.) and subcloned into the dephosphorylated plasmid Bluescript pKS(+) digested with EcoRV (see Ausubel et al. 1994, loc. cit.). The BglII/XhoI fragment was then cut out of the cloning vector via BglII and XhoI.

A 3-fragment ligation of ΔGAGXHO (digested with BglII and XhoI) was then carried out with the annealed, double-stranded splicing acceptor oligonucleotide (with the cutting sites SalI and NotI) in the base vector SFβ1 PSNEBH opened via BglII and NotI.

This resulted in the base vector SFβ71 NEBH.

EXAMPLE 3

Site-Directed Mutagenesis of AUG Sites

The 5'-untranslated region of SFβ71 NEBH still contains an ATG start codon. This was eliminated using a PCR-assisted site-directed mutagenesis (QuikChange site-directed mutagenesis Kit, Stratagene GmbH, Heidelberg, procedure according to the manufacturer's protocol). For this purpose, a PCR with the primers MUT/leader-ATG/+ (SEQ ID NO: 8) and MUT/leader-ATG/− (SEQ ID NO: 9) was carried out as follows:
Reaction Mixture:
  100 ng SFβ71 NEBH
  10 pmol primer MUT/leader-ATG/+
  10 pmol primer MUT/leader-ATG/−
  80 pmol/l dNTP
  5 μl 10× Pfu-PCR buffer
  1 μl native Pfu-DNA polymerase
    (Stratagene GmbH, Heidelberg)
  ad 50 μl H₂O The reaction mixture was first incubated at 95° C. for 5 min. 30 cycles were then carried out under the following conditions:
95° C. 30 s
55° C. 60 s
68° C. 10 min The reaction mixture was then incubated at 68° C. for 20 min.

The reaction product was then digested with DpnI for one hour and transformed into bacteria of the strain CMK by means of the calcium chloride method (see Ausubel et al. 1994, loc. cit.). The success of the mutagenesis was verified by means of sequencing.

This resulted in the base vector SFβ91 NEBH.

EXAMPLE 4

Site-Directed Mutagenesis of Cryptic Splicing Acceptor Sites, Splicing Donor Sites and Poly-A sites Cryptic splicing acceptor sites, splicing donor sites and poly-A sites in the MDR1 cDNA (Chen et al., Cell 47: 381–389 (1986), a sequence obtainable via EMBL Accession Number M 14758) were removed by means of site-directed mutagenesis (see above) with insertion of silent mutations (i.e. preserving the wild-type amino acid sequence).

In the following, for the experimental procedure described below, the first oligonucleotide is always primer A and the second oligonucleotide is always primer B.

The splicing donor consensus signal SD1 (position +339 of the MDR1 cDNA, mutation G to A) was mutated using the QuikChange site-directed mutagenesis kit (Stratagene) and the double-stranded oligonucleotides SD1+ (SEQ ID NO: 10) and SD1− (SEQ ID NO:11).

The splicing acceptor consensus signal SA1 (position +2320 of the MDR1 cDNA, mutation G to A) was mutated using the QuikChange site-directed mutagenesis kit (Stratagene) and the double-stranded oligonucleotides SA1+ (SEQ ID NO: 12) and SA1− (SEQ ID NO:13). The variant cDNA mSA1 resulted.

The polyadenylation consensus signal AATAAA1 (position +3303 of the MDR1 cDNA, mutation A to T) was mutated using the QuikChange site-directed mutagenesis kit (Stratagene) and the double-stranded oligonucleotides AATAAA+ (SEQ ID NO: 14) and AATAAA-(SEQ ID NO: 15).

All the mutageneses were carried out (apart from the particular primary pairs employed) under identical conditions in accordance with the manufacturer's instructions (QuikChange site-directed mutagenesis Kit, Stratagene GmbH, Heidelberg), a plasmid derived from pKS(+) (pKS ml) which contained the coding region of MDR1 being employed:

Reaction Mixture:
100 ng pKS ml
10 pmol primer A
10 pmol primer B
80 µmol/l dNTP
5 µl 10× Pfu-PCR buffer
1 µl native Pfu-DNA polymerase
ad 50 µl H$_2$O The reaction mixture was first incubated at 95° C. for 5 min. 30 cycles were then carried out under the following conditions:
95° C. 30 s
55° C. 60 S
68° C. 10 min The reaction mixture was then incubated at 68° C. for 20 min.

The MDR1 cDNA containing all these modifications was called "m4". By cloning the m4 cDNA into the base vector SFβ71 and by cloning the mSA1 cDNA into the base vector SPβ91, the constructions SFβ71m4 and SFβ91mSA1 (see FIG. 2), which transfer and express an MDR1 gene which is stable in the retroviral context, were acquired. These constructions can serve as the basis for bi- and oligocistronic MDR1 vectors, regardless of the choice of other regulatory elements.

EXAMPLE 5

Determination of the Titre of the Retroviral Expression Vector

Human MDR1 cDNA was used as the indicator gene. MDR1 cDNA was cloned into the vector SFβ11 NEBH and SFβ71 NEBH by means of standard methods (Ausubel et al., loc. cit.). For this, the 5'-untranslated portion of the cDNA was deleted exactly via PCR-directed cloning and the start codon of the MDR1 cDNA was provided with a Kozak consensus for optimization of the translation start and a prior restriction site for the enzyme NotI. The MDR1-carrying derivatives SFβ11m1 and SFβ71m1 resulted.

For analysis of the properties of SFβ11m1 and SFβ71m1 in respect of titre and translation efficiency, comparison vectors which also carry MDR1 under identical FMEV enhancer control, but with conventional untranslated sequences of the vector, were cloned. These are SFβ1m1 (LX type), SFβ6m1 (MFG type) or SP7m (LX type with splicing acceptor oligonucleotide) (see FIG. 3a).

The day beforehand, a confluent 9 cm dish of a virus producer (GP&AM12 American Type Culture Collection (ATCC CRL-9641)) was fed with 5 ml of fresh medium (IMDM+10% heat-inactivated foetal calf serum (FCS)). In parallel, 10,000 HT1080 (human fibrosarcoma cells, ATCC CRL-9641) were sown into each well of a 24-well plate. The following day, the virus-containing supernatant was subjected to sterile filtration through a 1.2 µm filter and serial 1:5 dilutions were prepared in IMDM+10% heat-inactivated FCS+4 µg/ml Polybrene® (hexadimethrine bromide, copolymer of N,N,N',N'-tetramethyl-1,6-hexanediamine and 1,3-dibromopropane; polycation for better interaction between the virus and cell on injection). Thereafter, the medium of the 24-well plate was removed and 1 ml of virus-containing supernatant of the corresponding dilution level was placed on top, in a triplicate determination, in accordance with the following plan:

| 1:5 | 1:5 | 1:5 | 1:3125 | 1:3125 | 1:3125 |
|---|---|---|---|---|---|
| 1:25 | 1:25 | 1:25 | 1:5625 | 1:5625 | 1:5625 |
| 1:125 | 1:125 | 1:125 | 1:78125 | 1:78125 | 1:78125 |
| 1:625 | 1:625 | 1:625 | no virus | no virus | no virus |

The following day, the medium was again removed from the 24-well plate and the cells were fed with IMDM+10% FCS +20 ng/ml colchicine. This was repeated every 2 days until there were no longer any living cells in the wells without virus supernatant.

The titre is obtained by multiplication of the number of clones in a certain well by the corresponding dilution level. For example, if at the 1:78125 dilution there is on average one clone in each well, the total titre would be 78125.

In these experiments it was found that the vectors according to the invention can be produced in high titres, it being possible for up to 5×10$^6$ infectious units to be achieved per ml.

EXAMPLE 6

Investigation of the Translation Efficiency

To investigate the translation efficiency of the vectors according to the invention, human K562 erythroleukaemia cells were infected with supernatants of vector-producing GP&envAM12 cells (ATCC CRL-9641) and polyclonal mass cultures were prepared by mild but background-free selection in 5 ng colchicine/ml cell culture medium. K562 cells which are transfected with retroviral vectors without MDR1 cDNA die under these conditions. The mass cultures were then cloned out in soft agar medium against increasing doses of colchicine.

For this, IMDM+10% FCS and 0.33% Bacto-Agar was first prepared. The medium was then adjusted by addition of colchicine to a final concentration of
a) 20 ng/ml colchicine
b) 40 ng/ml colchicine
c) 60 ng/ml colchicine.

Thereafter, 500 K562 per ml medium were added and in each case 1 ml was pipetted into a well of a 12-well plate in accordance with the following plan:

| 500 K562 0 ng/ml colchicine | 500 K562 0 ng/ml colchicine | 500 K562 0 ng/ml colchicine |
|---|---|---|
| 500 K562 20 ng/ml colchicine | 500 K562 20 ng/ml colchicine | 500 K562 20 ng/ml colchicine |
| 500 K562 40 ng/ml colchicine | 500 K562 40 ng/ml colchicine | 500 K562 40 ng/ml colchicine |
| 500 K562 60 ng/ml colchicine | 500 K562 60 ng/ml colchicine | 500 K562 60 ng/ml colchicine |

After brief incubation at 4° C. (agar solidifies), the plates were incubated for 14 days at 37° C. and 5% CO$_2$. After 14 days, the number of living colonies per well was determined. The relative cloning efficiency is obtained by division of the average number of clones at a certain colchicine concentration by the average number of clones without colchicine addition.

The cloning efficiency in the presence of high colchicine doses is a very sensitive indicator of the expression level of MDR1 [C. Baum et al. (1995) J. Virol. 69: 7541–7547]. The constructions according to the invention (SFβ11m1 and SFβ71m1) achieved a significant (2.5-fold) increase in the cloning efficiency compared with the LX type standard vector (SFβ1m1), the activity of which has been set at 1 (see FIG. 3B). The vectors according to the invention were also superior to the positioning realized in the MFG vector with splicing acceptor oligonucleotide (SFβ7m1) instead of the viral env gene (SFβ6m1) or the SFβ1m1 variant. In these experiments it was found that the vectors according to the invention impart an improved gene expression. This is probably based on increased post-transcriptional efficiency (increase in the translation efficiency), since the vectors used were identical in respect of the transcriptional control regions.

EXAMPLE 7

Expression of Humanized Enhanced Preen Fluorescent Protein by Means of the Retroviral Vectors According to the Invention The transgene humanized enhanced green fluorescent protein (abbreviated to eGFP; CLONTECH GmbH, Heidelberg) was cloned into the vectors SFβ1, SFβ6, SFβ71 and SFβ91 according to the invention. The expression of the transgene in the erythroleukaemic cell line K562 was analysed by flow-through cytometry.

a) Cloning of SFβ1eGFP/SFβ6eGFP/SFβ71eGFP/ SFβ91eGFP eGFP was amplified via PCR with the vector pEGFP-C1 (CLONTECH GmbH, Heidelberg) as the matrix using the primers eGFP+ (SEQ ID NO: 16) and eGFP− (SEQ ID NO: 17):

Reaction Mixture:
10 ng pEGFP-C1
50 pmol primer eGFP
50 pmol primer eGFP
80 μmol/l dNTP
10 μl 10× Pfu-PCR buffer
1 μl recombinant Pfu-DNA polymerase
(Stratagene GmbH, Heidelberg)
ad 100 μl H$_2$O The reaction mixture was first incubated at 95° C. for 5 min. 30 cycles were then carried out under the following conditions:
95° C. 30 s
55° C. 40 s
72° C. 2 min
The reaction mixture was then incubated at 72° C. for 10 min.

The resulting product (eGFP) was phosphorylated by means of adenosine triphosphate (see Ausubel et al. 1994, loc. cit.) and subcloned into the dephosphorylated plasmid Bluescript pKS(+) digested with EcoRV (see Ausubel et al. 1994, loc. cit.). eGFP was then cut out of the cloning vector via NotI and EcoRI and inserted into the base vectors, each of which were linearized via a restriction digestion with the enzymes NotI and EcoRI and then dephosphorylated by means of bovine alkaline phosphatase (see Ausubel et al. 1994, loc. cit.). This resulted in the vectors SFβ1eGFP/ SFβ6eGFP/SFβ71eGFP/SFβ91eGFP.

b) Recording of Data

The amphotropic packing cell lines GP&Am12 was transfected with 10 μg plasmid-DNA of SFβ1eGFP, SFβ6eGFP, SFβ71eGFP or SFβ91eGFP by means of calcium phosphate precipitation (see Ausubel et al. 1994, Current protocols in molecular biology, John Wiley & Sons, New York, N.Y., USA). One day after the transinfection, virus-containing supernatant was harvested and K562 cells were infected. After a further three days, the eGFP expression of the K562 was analysed by flow-through cytometry using a FACScalibur (Becton Dickinson GmbH, Heidelberg) and the average fluorescence of the expressing K562 was determined. The values shown in FIG. 4 were obtained (based on SFβ1eGFP).

EXAMPLE 8

Evidence of the Stability of the Modified MDR1 cDNA

The evidence of the stability of the modified MDR1 cDNAs "mSA1" and "m4" was provided via flow-through cytometry of K562 mass cultures which had been transduced retrovirally with MDR1 vectors without selection beforehand for intactness of the MDR1 cDNA. For this, a gene cassette which carries 3' of the MDR1 cDNA of the neomycin resistance gene (neoR) under control of a retroviral splicing acceptor (derived from SF1MSN [M. Hildinger et al., loc. cit.] was introduced into SFβ71m4 and SFβ91mSA1. The resulting vectors were called SFβ91mSA1SN and SFβ71m4SN. Transduced cells were selected with G418 (geneticin), against which neoR imparts resistance.

For the Rh123 efflux assay, 10$^6$ K562 were incubated in 2 ml medium with 10 μg/ml Rh123 for 30 min at 37° C. After washing twice with 5 ml PBS each time, the cells were incubated for a further 2 hours in 2 ml medium at 37° C. During this period, Rh123 was sluiced out of the cells. After two further washing steps, the cells were taken up in 1 ml PBS and analysed on a FACS-Analyser from Becton-Dickinson (FACSCalibur), the Rh123 fluorescence being measured on fluorescence channel 1. If the cells express MDR1, Rh123 is sluiced out of the cells and the fluorescence of the cells is correspondingly lower.

In the context of these experiments it became clear that on transduction with SFβ91mSA1SN or SFβ71m4SN, few or no MDR1-defective cells occur, while on transduction with SFβ1mSN, approx. 40% MDR1-defective cells are to be recorded (see FIG. 5). These defects are based on genetic rearrangements of the cDNA, which are suppressed by elimination of the processing signals in the m4 or mSA1 variant.

LX and MFG contain the gag+sequences (gagA), and MFG additionally also parts of pol (polΔ). Transcription control is by the LTR, especially the enhancer/promoter sequence in the U3 region. Translation of the transgene is preferably via spliced variants of the vector RNA, which are formed by recognition of the splicing donor (SD) and splicing acceptor (SA) sites. The arrow above the vector DNA represented as a symbol indicates the vector RNA, and the broken portions relate to the portions of the transcript removed by splicing. The transgene (cDNA) starts at the LX vector in the middle of the gag region, and all the other virus-coding sequences are eliminated. Parts of the pol sequences present in the MFG vector contain the splicing acceptor of the env gene. In both cases (LX and MPG), the start codon of the gag gene is destroyed (AUG crossed out), but there are multiple further AUGs in all the reading frames upstream of the transgene.

In the particularly preferred embodiment of the vector according to the invention, all the virus-coding sequences are eliminated. The vector has therefore been called gagpol-env-deleted vector (GDV). Only cis-regulatory portions of the virus are still present (LTRs with U3, R and U5 and the packing region (Ψ).

Figure 1:
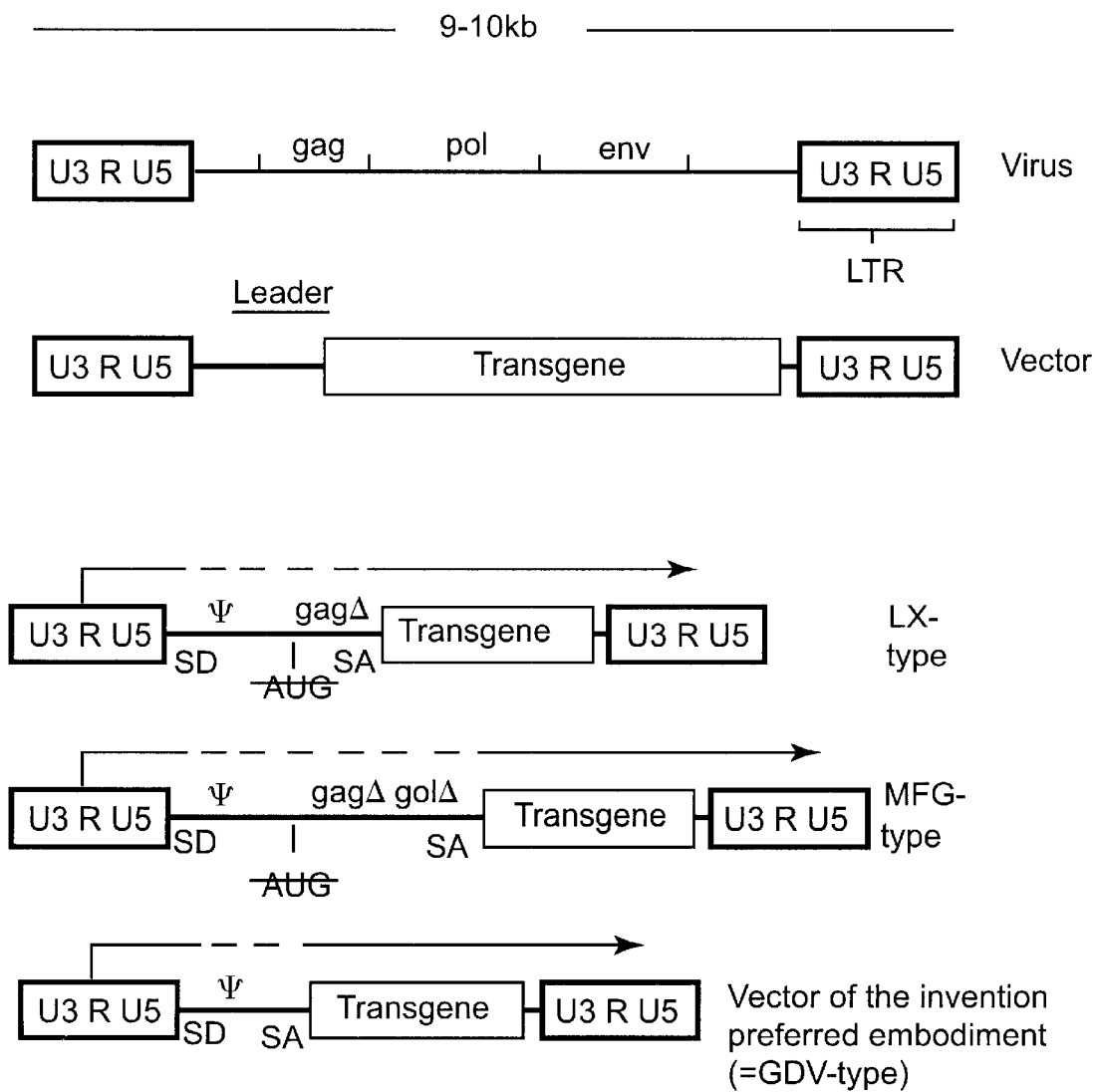
FIG. 1 Comparison of retroviral vectors of the type LX and MFG with the new form.
Figure 2:
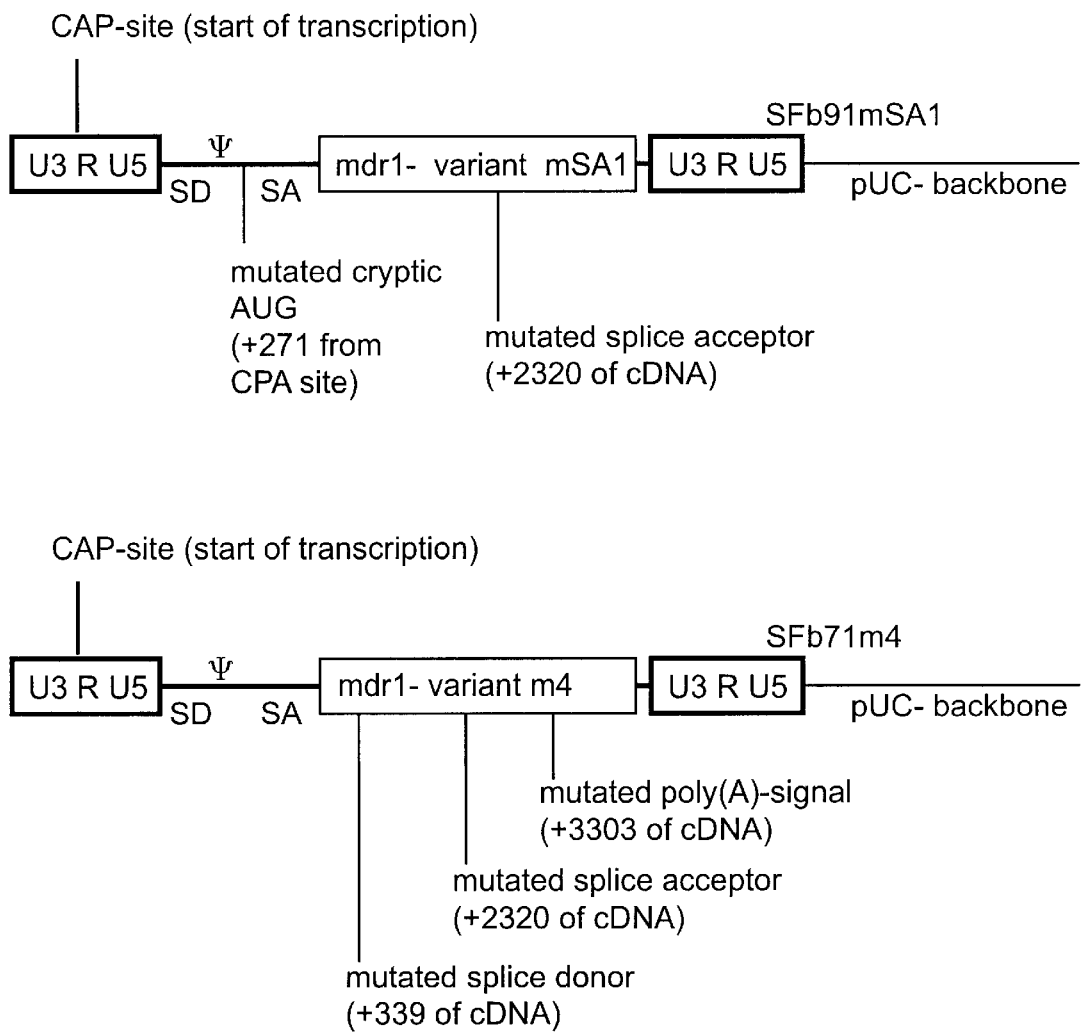

FIG. 2 Vectors SFβ91mSA1 and SFβ71m4 according to the invention, a diagram of the proviral form. The vectors contain no coding sequences of the retrovirus. The transcription of the viral RNA starts at the CAP site. The plasmid backbone originates from the cloning vector pUC19 (New England Biolabs) and has no influence on the function of the retroviral vector.

Figure 3A:
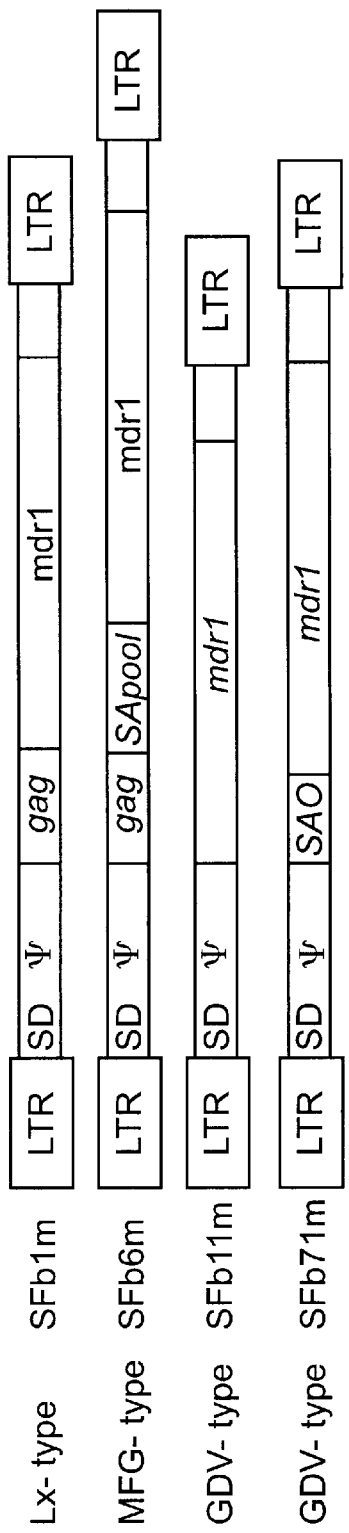
Figure 3B:
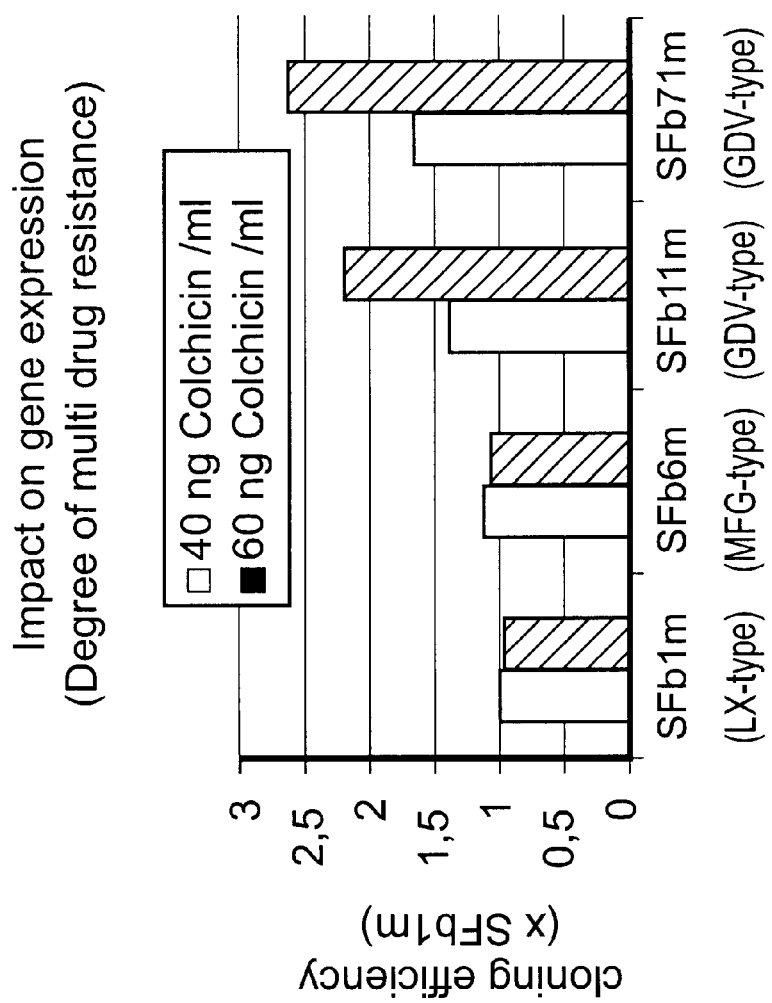

FIG. 3 Influence of the new vector construction (GDV type) on the intensity of the gene expression, in this example: Improvement of the vector-mediated multidrug resistance in the high-dose range.
A: Vector construction. SD: Splicing donor of the vector; gag: gag gene fragment; SApol: Splicing acceptor-containing pol fragment, SAC: Splicing acceptor oligonucleotide
B. Cloning efficiency (mean of 3 experiments, standard deviations were less than 25%)

Figure 4A:
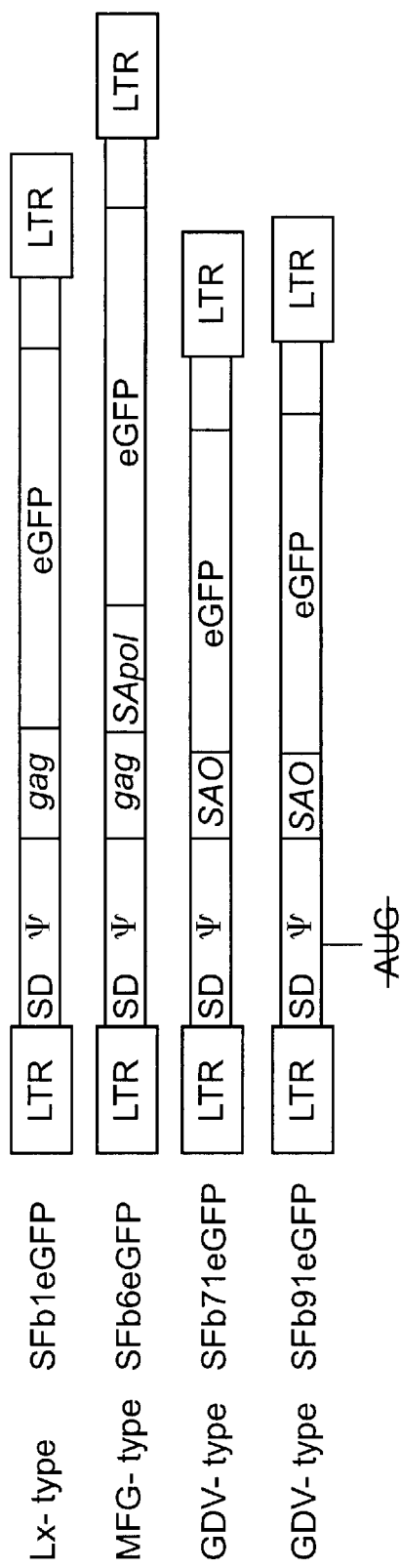
Figure 4B:
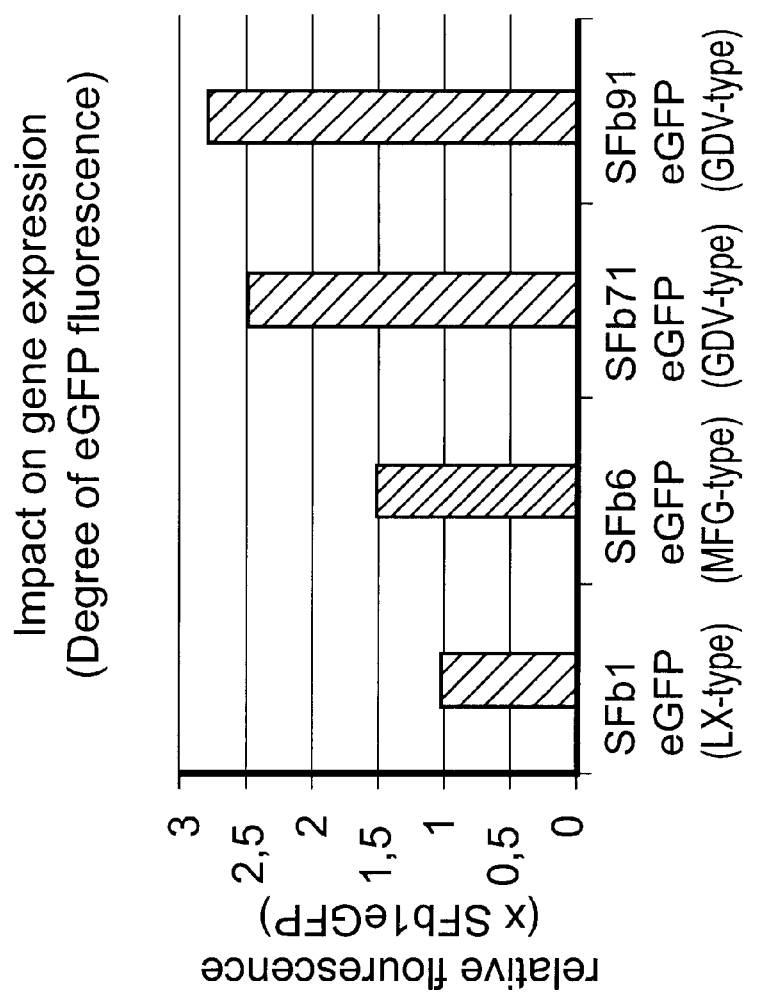

FIG. 4 Influence of the new vector construction (GDV type) on the intensity of the gene expression, in this example: Increase in the eGFP fluorescence in transduced cells.
A: Vector construction,
B: Average fluorescence (mean of more than 10,000 events)

Figure 5A:
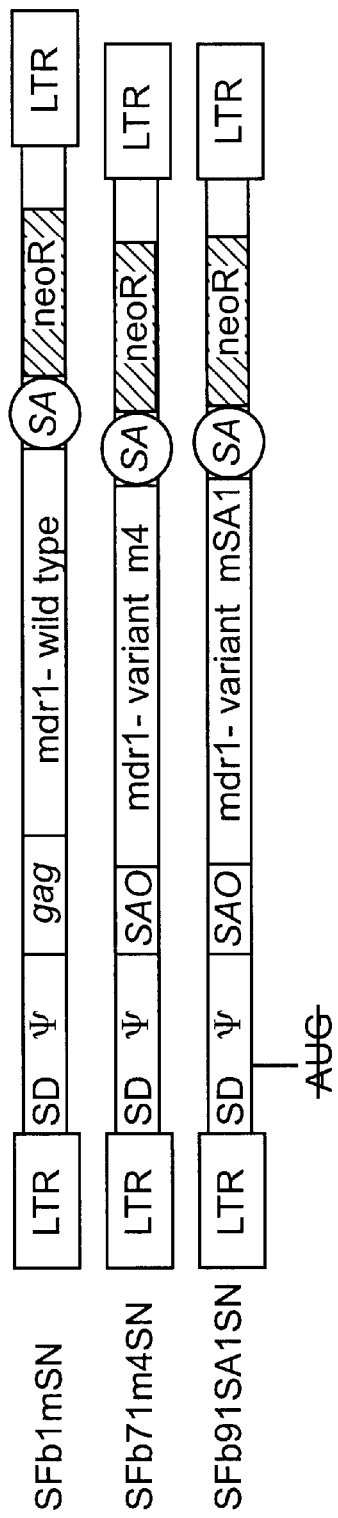
Figure 5B:
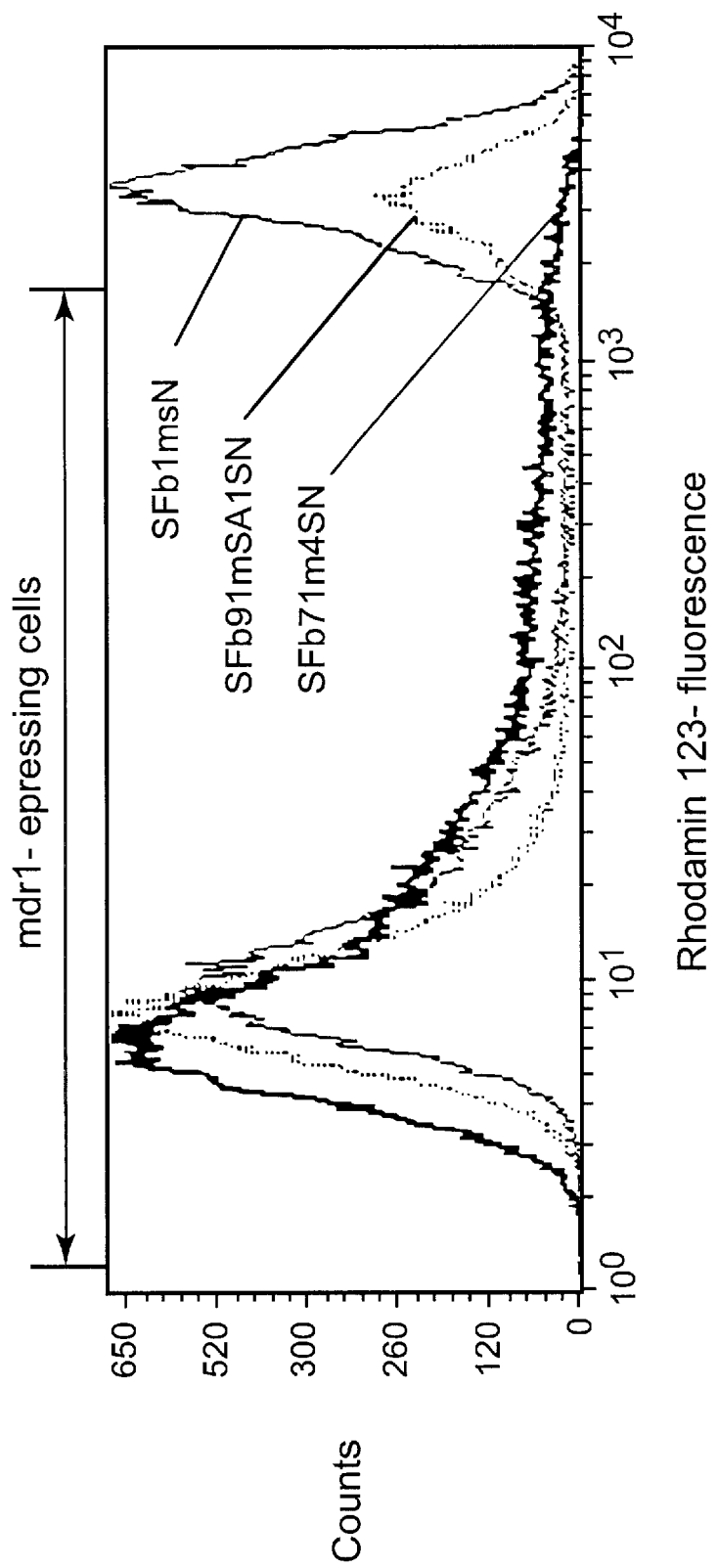

FIG. 5 Removal of aberrant slicing from the MDR1 cDNA
A: Vectors with which K562 cells were transduced followed by selection with G418 (resistance via the neoR gene of the vector).
B: Rhodamine 123 efflux experiment with which the integrity of the MDR1 cDNA in the G418-selected mass culture is detected (Hildinger et al. (1997) Hum. Gene Ther. 9: 33–42).

In the case of SFβ91mSA1SN, the MDR1 cDNA is partly, and in the case of SFβ71m4SN completely intact.

This shows that the internal splicing of the MDR1 cDNA is prevented before the reverse transcription. The increased expression of MDR1 also manifests itself in the histogram peak shifted further to the lower fluorescence.

What is claimed is:

1. A retroviral vector which contains a nucleotide sequence N of the general formula 5'-end—(5'-UTR)-(gag)-(ex)-(vir)—3'-end wherein
the presence of (gag) is optional,
(5'-UTR) is a non-coding nucleotide sequence which in retroviruses lies directly 5' of the start codon of the gag gene,
(gag) is, when present, a section of the nucleotide sequence which codes for the gag gene,
(ex) is a non-viral nucleotide sequence and
(vir) is a retroviral nucleotide sequence,
wherein
the number of nucleotides in (gag) is less than 400 bp, and the vector contains no ATG or AUG upstream of the translation start of the sequence in (ex).

2. The vector according to claim 1, wherein the number of nucleotides in (gag) is less than 200 bp.

3. The vector according to claim 1, wherein (gag) is not present.

4. The vector according to claim 1, which additionally contains at least one sequence which codes for the Pro protein, the Env protein, the Pol protein or another viral protein.

5. The vector according to claim 1, wherein the nucleotide sequence (ex) contains at least one nucleotide sequence which codes for a non-viral protein, or a non-translated, non-viral RNA.

6. The vector according to claim 5, wherein the first nucleotide of the start codon of the nucleotide sequence which codes for a non-viral protein is the 5'-end of the nucleotide sequence (ex).

7. The vector according to claim 1, wherein the nucleotide sequence (ex) additionally contains regulatory nucleotide sequences.

8. The vector according to claim 7, wherein the regulatory nucleotide sequences are at least one of splicing acceptor sites, promoter sequences or enhancer sequences.

9. The vector according to claim 1, wherein (5'-UTR) contains at least one sequence section which is a splicing acceptor.

10. The vector according to claim 9, wherein the splicing acceptor is an oligonucleotide with a length of 10 to 150 bp.

11. The vector according to claim 1, wherein (5'-UTR) contains no nucleotide triplet with the sequence ATG.

12. The vector according to claim 1, wherein the nucleotide sequences in the nucleotide sequence (ex) which code for non-viral proteins do not contain at least one of cryptic splicing donor sites, splicing acceptor sites or cryptic poly-A sites.

13. The vector according to claim 1, wherein 5' of (ex) lies a leader region.

14. The vector according to claim 13, (wherein the leader region originates from MESV.

15. The vector according to claim 1, wherein 3' of (vir) lies a 3'-LTR.

16. The vector according to claim 15, wherein the 3'-LTR originates from spleen focus forming virus (SFFVp).

17. The vector according to claim 1, wherein the nucleotide sequence lying in the nucleotide sequence (ex) codes for the MDR1 protein.

18. The vector according to claim 17, which is DSM 12065 or DSM 12066 deposited under the conditions of the Budapest Treaty on Mar. 20, 1998 at the Deutsche Sammlung von Mikroorganismen und Zellkulturen [German Collection of Microorganisms and Cell Cultures], Masoheroder Weg 1b, 38124 Braunschweig.

19. The vector according to claim 17, which is the vector deposited under DSM 12065 deposited under the conditions of the Budapest Treaty on Mar. 20, 1998 at the Deutsche Sammlung von Mikroorganismen und Zellkulturen [German Collection of Microorganisms and Cell Cultures], Maccheroder Web 1b, 38124 Braunschweig, wherein
   a) It contains no nucleotide sequences which code for viral proteins,
   b) it contains the U3, R and U5 regions of the 5'-LTR at the 5'-end of the proviral DNA,
   c) the CAP site at which the transcription of the viral mRNA starts lies in the 5'-LTR,
   d) 3' of the 5'-LTR lies a nucleotide sequence which contains a splicing acceptor, a packing region (Ψ) and a splicing donor, nucleotide 271 (counted from the CAP site) being mutated in order to remove a cryptic AUG,
   e) at the site at which the sequences which code for the gag gene were to be found, it contains the variant mSA1 of the MDR1 gene, a cryptic splicing acceptor being mutated at position 2320 (counted from the start codon of the MDR1 gene), and
   f) 3' of the MDR1 variant mSA1 is the 3'-LTR with the U3, R and U5 regions.

20. The vector according to claim 17, which is the vector deposited under DSM 12066 deposited under the conditions of the Budapest Treaty on Mar. 20, 1998 at the Deutsche Sammlung von Mikroorganismen und Zellkulturen [German Collection of Microorganisms and Cell Cultures], Masoheroder Weg 1b, 38124 Braunschweig, wherein
   a) it contains no nucleotide sequences which code for viral proteins,
   b) it contains the U3, R and U5 regions of the 5'-LTR at the 5'-end of the proviral DNA,
   c) the CAP site at which the transcription of the viral RNA starts lies in the 5'-LTR,
   d) 3' of the 5' LTR lies a nucleotide sequence which contains a splicing acceptor, a packing region (Ψ) and a splicing donor,
   e) at the site at which the sequences which code for the gag gene were to be found, it contains the variant m4 of the MDR1 gene, a cryptic splicing donor being mutated at position 339 (counted from the start codon of the MDR1 gene), a cryptic splicing acceptor being mutated at position 2320 (counted from the start codon of the MDR1 gene) and a cryptic poly(A) signal being mutated at position 3303 (counted from the start codon of the MDR1 gene), and
   f) 3' of the MDR1 variant m4 is the 3'-LTR with the U3, R and U5 regions.

21. The vector according to claim 1, wherein
   a) the nucleotide sequence lying in the nucleotide sequence (ex)codes for the MDR1
   b) it contains no nucleotide sequences which code for viral proteins,
   c) it contains the U3, R and U5 regions of the 5'-LTR at the 5'-end of the proviral DNA,
   d) the CAP site at which the transcription of the viral RNA starts lies in the 5'-LTR,
   e) 3' of the 5' LTR lies a nucleotide sequence which contains a splicing acceptor, a packing region (Ψ) and a splicing donor,
   f) at the site at which the sequences which code for the gag gene were to be found, it contains the variant m4 of the MDR1 gene, a cryptic splicing donor being mutated at position 339 (counted from the start codon of the MDR1 gene), a cryptic splicing acceptor being mutated at position 2320 (counted from the start codon of the MDR1 gene) and a cryptic poly(A) signal being mutated at position 3303 (counted from the start codon of the MDR1 gene),
   g) 3' of the MDR1 variant m4 Is the 3'-LTR with the U3, R and U5 regions, and
   h) it contains a mutated cryptic AUG at position 271 (counted from the CAP site).

22. A process for obtaining an infectious virus particle, comprising transfecting a packing-competent helper cell with a retroviral vector according to claim 1 and culturing the helper cell in a suitable medium under conditions which are suitable for release of Infectious virus particles which contain the retroviral vector as the genome.

23. An infectious virus particle which contains the retroviral vector according to claim 10.

24. A host cell, which is transfected in vitro with the retroviral vector according to claim 1.

25. A host cell which is infected in vitro with an infectious virus particle according to claim 23.

26. The host cell according to claim 24, which is transfected in vitro with a vector corresponding to DSM 12065 or DSM 12066 deposited under the conditions of the Budapest Treaty on Mar. 20, 1998 at the Deutsche Summlung von Mikroorganismen und Zellkulturen [German Collection of Microorganisms and Cell Cultures], Mascheroder Web 1b, 38124 Braunschweig.

27. A method of expression cloning of proteins or RNA comprising contacting infectious virus particles which contain the retroviral vector according to claim 1 with suitable host cells under conditions which allow infection of cells, and culturing the infected cells under conditions which allow expression of the protein encoded by the non-viral nucleotide sequence.

28. A method of at least one of expression or overexpression of proteins or RNA comprising containing infectious virus particles which contain the retroviral vector according to claim 1 with suitable host cells under conditions which allow infection of cells, and culturing the infected cells under conditions which allow expression of the protein encoded by the non-viral nuoleotide sequence.

29. A method of transfection of haematopoietic stem cells comprising contacting infectious virus particles containing the retroviral vector according to claim 1 with haematopoietic stem cells under conditions which allow infection of the cells.

30. A process for obtaining proteins, wherein a host cell according to claim 24 is cultured in a suitable medium under conditions which are necessary for expression of the non-viral proteins for which nucleotide sequence in (ex) code, and wherein the protein produced is removed from the cells and the medium.

31. A method of transfection of haematopoietic stem cells comprising contacting infectious virus particles containing the retroviral vector according to claim 17 with hematopoietic stem cells under conditions which allow infection of the cells.

32. An isolated haematopoietic stem cell comprising the retroviral vector according to claim 1.

33. An isolated haematopoietic stem cell comprising the retroviral vector according to claim 17.

* * * * *